United States Patent
Kobayashi et al.

(10) Patent No.: US 6,218,439 B1
(45) Date of Patent: Apr. 17, 2001

(54) METHOD OF MANUFACTURING METHANOL

(75) Inventors: Kazuto Kobayashi; Hideaki Nagai, both of Tokyo; Hiroyuki Osora, Hiroshima; Yoshio Seiki, Hiroshima; Tetsuya Imai, Hiroshima, all of (JP)

(73) Assignee: Mitsubishi Heavy Industries, Ltd., Tokyo (JP)

( * ) Notice: Subject to any disclaimer, the term of this patent is extended or adjusted under 35 U.S.C. 154(b) by 0 days.

(21) Appl. No.: 09/456,145

(22) Filed: Dec. 7, 1999

(30) Foreign Application Priority Data

Dec. 7, 1998 (JP) .................................................. 10-347460
Dec. 7, 1998 (JP) .................................................. 10-347461
Jul. 29, 1999 (JP) .................................................. 11-215226
Jul. 29, 1999 (JP) .................................................. 11-215227

(51) Int. Cl.[7] .................................................. C07C 27/00

(52) U.S. Cl. .......................... 518/713; 518/702; 518/703; 518/704

(58) Field of Search .................................. 518/702, 703, 518/704, 713

(56) References Cited

U.S. PATENT DOCUMENTS 5,063,250  11/1991  Murayama et al. .
5,631,302   5/1997  König et al. .

FOREIGN PATENT DOCUMENTS 1580390  9/1969  (FR) .
  51930  2/1942  (NL) .

OTHER PUBLICATIONS

"Meting Today's Challenges" *Nitrogen* 207: 27–28, 1994.
"Increased Production from Existing Methanol Plants," by A. English, I.A Forbes, M.N. Islam, J.D. Korchnak, presented to World Methanol Conference, Dec. 2–4, 1991, Hyatt Regency Hotel Vancouver, BC, Canada, p. 1–12.

*Primary Examiner*—Johann Richter
*Assistant Examiner*—J. Parsa
(74) *Attorney, Agent, or Firm*—John P. White; Cooper & Dunham LLP

(57) ABSTRACT

A raw material gas containing hydrocarbon as a main component is supplied together with steam to a reformer through a moistening device to form a synthetic gas containing hydrogen, carbon monoxide and carbon dioxide as main components by the reaction between the hydrocarbon contained in the raw material gas and the steam. In forming the synthetic gas, carbon dioxide is supplied to at least one fluid passageway selected from the group consisting of the fluid passageway positioned upstream of the moistening device and the fluid passageway interposed between the moistening device and the reformer. As a result, the excess hydrogen contained in the gas formed in the reformer is effectively utilized without bringing about deactivation of the methanol synthesizing catalyst in the methanol synthesizing step. Also, carbon dioxide is effectively utilized to decrease the amount of carbon dioxide discharged to the outside of the system. Further, it is possible to decrease the amount of steam supplied to the reformer.

12 Claims, 6 Drawing Sheets

METHOD OF MANUFACTURING METHANOL

BACKGROUND OF THE INVENTION

The present invention relates to a method of manufacturing methanol, particularly, to a method of manufacturing methanol in which carbon dioxide is utilized for increasing the methanol yield.

Japanese Patent Disclosure (Kokai) No. 1-180841 discloses a method of manufacturing methanol ($CH_3OH$) from hydrocarbons such as natural gas by the processes described below:

(Synthetic Gas-Forming Process)

In the first step, a synthetic gas containing as main components hydrogen ($H_2$), carbon monoxide (CO) and carbon dioxide ($CO_2$) is formed in a reformer by the reaction between a natural gaseous hydrocarbon or a gaseous hydrocarbon evaporated from a liquid hydrocarbon and steam at a predetermined temperature in the presence of a nickel-based catalyst.

Steam is added to the hydrocarbon from a moistening device arranged upstream of the reformer, followed by supplying a superheated steam prepared in a boiler or the like to the hydrocarbon so as to introduce a gaseous mixture containing hydrocarbon and steam into the reformer.

Since the steam reforming reaction noted above is an endothermic, reaction accompanied by a large amount of reaction heat, the reformer is heated from the outside in the process of forming the synthetic gas.

(Crude Methanol Synthetic Process)

A crude methanol is synthesized by the reaction among the synthetic gas, carbon monoxide and hydrogen or among the synthetic gas, carbon dioxide and hydrogen at a predetermined pressure and temperature in the presence of a methanol synthesizing catalyst to synthesize a crude methanol.

(Distilling Process)

The liquid crude methanol recovered in the methanol synthesizing process is distilled in a single or a plurality of distillation columns so as to separate the crude methanol into a waste liquid material and a refined methanol, said waste liquid material containing organic compounds having melting points lower than that of methanol (hereinafter referred to as "low boiling point organic compound"), organic acids and organic compounds having boiling points higher than that of methanol (hereinafter referred to as "high boiling point organic compound").

Methanol is manufactured via the processes described above.

In recent years, it is of high importance to suppress the amount of carbon dioxide discharged from a plant as a measure against warming of the earth.

In a plant for manufacturing methanol from hydrocarbon such as natural gas, the heat required for the endothermic reaction between carbon monoxide and hydrogen is supplied to the reformer by heating the reaction tube loaded with a steam reforming catalyst with a combustion gas. Also, a boiler for steam generation is used for replenishing a required amount of a high pressure steam consumed in the plant. Naturally, a large amount of carbon dioxide is contained in the combustion waste gas of the reformer and the boiler for the steam generation. It follows that the plant tends to be rendered disadvantageous in economy where a tax and regulation for the carbon dioxide discharge are started in future.

On the other hand, in the method of manufacturing methanol from natural gas, the hydrogen concentration in the synthetic gas formed by the steam reforming reaction is about 1.5 times as high as that required for synthesizing methanol by the reaction of hydrogen with carbon monoxide and carbon dioxide contained in the synthetic gas. Therefore, in the process of synthesizing methanol, the unreacted gas separated from the synthesized methanol is recycled to the synthesizing reactor in order to improve the reaction efficiency within the synthesizing reactor, and the unreacted gas is partly released to the outside of the system to release the excess hydrogen. Also, the recycling amount of the unreacted gas is set at a value which permits moderating the heat generation rate during reaction in the catalyst layer loaded in the synthesizing reactor.

Under the circumstances, the idea of supplying carbon dioxide to a fluid passageway through which a synthetic gas formed in a reformer is supplied to the methanol synthesizing reactor is shown in FIG. 5 of "INCREASED PRODUCTION FROM EXISTING METHANOL PLANTS BY A. English, I. A. Forbes, M. N. Islam, J. D. Korchank PRESENTED TO: WORLD METHANOL CONFERENCE Dec. 2–4, 1991 HYATT REGENCY HOTEL VANCOUVER, BC, CANADA, pp. 1–12".

However, if a synthetic gas containing a large amount of carbon dioxide is supplied to the reactor in the crude methanol synthesizing step, the activity of the methanol synthesizing catalyst loaded in the reactor tends to be lowered.

BRIEF SUMMARY OF THE INVENTION

An object of the present invention is to provide a methanol manufacturing method capable of effectively utilizing an excess hydrogen in the mixed gas formed in the reformer to increase the methanol yield without bringing about reduction in the activity of the methanol synthesizing catalyst in the methanol synthesizing step, capable of effectively utilizing carbon dioxide so as to decrease the discharged amount of carbon dioxide, and also capable of decreasing the amount of steam supplied from outside into the reformer.

Another object is to provide a methanol manufacturing method capable of effectively utilizing the unreacted gas in the methanol synthesizing step so as to increase the methanol yield, and also capable of effectively utilizing carbon dioxide so as to decrease the discharged amount of carbon dioxide.

According to a first aspect of the present invention, there is provided a method of manufacturing methanol, comprising the steps of:

supplying a raw material gas containing hydrocarbon as a main component and steam into a reformer, the raw material gas being supplied into the reformer through a moistening device, to carry out reaction between the hydrocarbon and steam to form a synthetic gas containing as main components hydrogen, carbon monoxide, and carbon dioxide;

performing reaction of the synthetic gas in the presence of a methanol synthesizing catalyst to synthesize a crude methanol; and distilling a liquid crude methanol recovered in the synthesizing process to separate the crude methanol into a waste liquid material and a refined methanol, the waste liquid material containing low boiling point organic compounds and high boiling point organic compounds, wherein carbon dioxide is supplied to at least one fluid passageway selected from the group consisting of a fluid passageway positioned upstream of the moistening device and another fluid passageway interposed between the moistening device and the reformer.

In the methanol manufacturing method of the present invention, it is possible for the moistening device to include a first stage moistening device and a second stage moistening device arranged downstream of the first stage moistening device and upstream of the reformer such that hydrocarbon and carbon dioxide are supplied to a fluid passageway positioned upstream of the first stage moistening device, and the waste liquid material recovered in the distilling process is supplied to a circulating water passageway of the first stage moistening device.

It is also possible to supply an additional carbon dioxide to at least one fluid passageway selected from the group consisting of a fluid passageway interposed between the first and second moistening devices and another fluid passageway interposed between the second stage moistening device and the reformer.

In the methanol manufacturing method of the present invention, it is desirable to use carbon dioxide recovered from at least one combustion gas selected from the group consisting of the combustion gas for heating the reformer and the combustion gas for heating a boiler for steam generation.

In the methanol manufacturing method of the present invention, it is desirable to use in the step of synthesizing the crude methanol a reaction apparatus comprising a reactor and a triple pipe consisting of an outer pipe, an intermediate pipe and an inner pipe that are concentrically arranged. The reactor is vertically partitioned by two partition plates into three chambers consisting of a synthetic gas supply chamber, a cooling medium circulating chamber and a residence chamber of the methanol-containing gas. The triple pipe extends through the two partition plates and is arranged such that the upper end of the intermediate pipe is positioned lower than the upper end of the outer pipe, that the lower end of the inner pipe is positioned in a central portion of the intermediate pipe, that the inner pipe alone is open in the upper end of the triple pipe, and that an annular space is formed between the intermediate pipe and the outer pipe in the lower end of the triple pipe, the methanol synthesizing catalyst being loaded in the annular space.

In the methanol manufacturing method of the present invention, it is desirable for the methanol synthesizing catalyst to consist of oxides of Cu, Zn, Al, Ga and M, which is at least one element selected from the alkaline earth metal elements and the rare earth elements, these Cu, Zn, Al, Ga and M being mixed at an atomic ratio of 100:10 to 200:1 to 20:1 to 20:0.1 to 20.

According to a second aspect of the present invention, there is provided a method of manufacturing methanol, comprising the steps of:

supplying a raw material gas containing hydrocarbon as a main component and steam into a reformer for the reaction to generate a synthetic gas containing as main components hydrogen, carbon monoxide and carbon dioxide;

performing reaction of the synthetic gas in the presence of a methanol synthesizing catalyst to synthesize a crude methanol; and distilling a liquid crude methanol recovered from the methanol synthesizing step to separate the crude methanol into a refined methanol and a waste liquid material containing low boiling point organic compounds and high boiling point organic compounds, wherein the methanol synthesizing step comprises a first reaction step and a second reaction step, reaction of the synthetic gas supplied through a synthetic gas supply passageway being carried out in the first reaction step in the presence of the methanol synthesizing catalyst, and wherein the formed liquid crude methanol containing unreacted gas is separated into a gaseous portion and a liquid portion, the liquid crude methanol is recovered, the unreacted gas is compressed and recycled to the synthetic gas supply passageway, a part of the compressed unreacted gas is mixed with carbon dioxide, and the mixed gas is introduced into the second reaction step so as to carry out the reaction of the mixed gas in the presence of the methanol synthesizing catalyst to form a crude methanol.

In the methanol manufacturing method according to the second aspect of the present invention, it is also possible to supply an additional carbon dioxide to the inlet port of the first reaction step.

In the methanol manufacturing method according to the second aspect of the present invention, the carbon dioxide to be supplied should desirably be carbon dioxide recovered from at least one of the combustion gases for heating the reformer and for heating the boiler for steam generation.

In the methanol manufacturing method according to the second aspect of the present invention, it is desirable for the methanol synthesizing catalyst to consist of oxides of Cu, Zn, Al, Ga and M, which is at least one element selected from the alkaline earth metal elements and the rare earth elements, these Cu, Zn, Al, Ga and M being mixed at an atomic ratio of 100:10 to 200:1 to 20:1 to 20:0.1 to 20.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments given below, serve to explain the principles of the invention.

DETAILED DESCRIPTION OF THE INVENTION

The methanol manufacturing method of the present invention will now be described in detail with reference to the accompanying drawings.

(First Embodiment)

Figure 1:
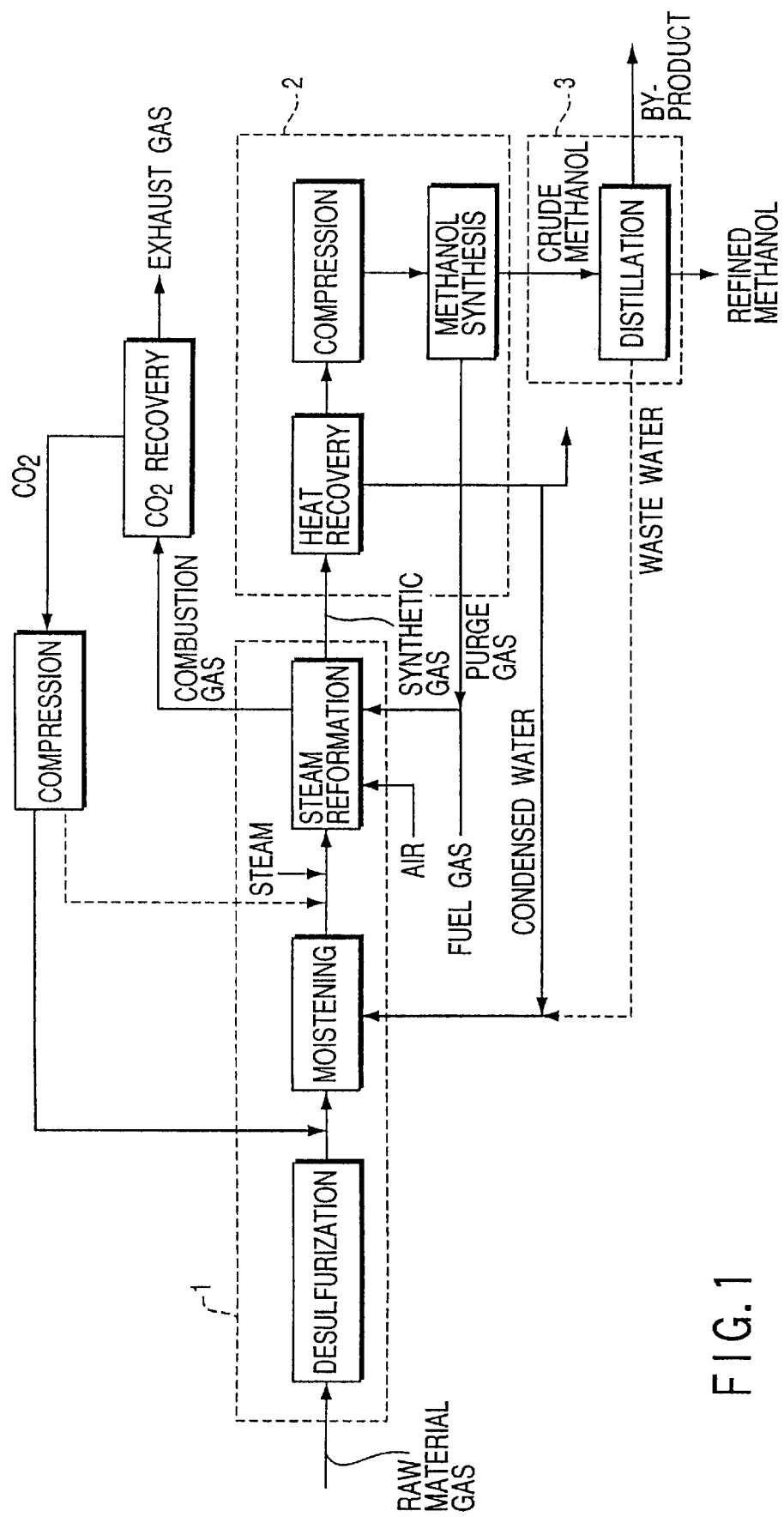
FIG. 1 is a flow chart showing a methanol manufacturing process of the present invention.

FIG. 1 is a flow chart showing a methanol manufacturing process according to a first embodiment of the present invention. As shown in the drawing, the process of the first embodiment comprises a synthetic gas forming step 1, a methanol synthesizing step 2 and a distilling step 3.

(1) Synthetic Gas Forming Step

As shown in the drawing, a raw material gas containing hydrocarbon as a main component, e.g., a natural gas, is supplied to a desulfurization device for removing traces of sulfur compounds contained in the raw material gas. After the desulfurization, the raw material gas is introduced into a moistening device, in which steam is added at, for example, 150 to 250° C. to the raw material gas to reach substantially a saturated pressure.

Then, a superheated steam prepared in, for example, a boiler is supplied to the moistened raw material gas and, then, the raw material gas is introduced into a reformer. It is desirable for the amount of steam contained in the mixed gas introduced into the reformer to be about 2 to 3 times as large as the volume flow rate of the raw material gas.

The raw material gas introduced into the reformer is reformed with steam introduced into the reformer together with the raw material gas at 800 to 1,000° C. in the presence of, for example, a nickel-based catalyst loaded in the reformer so as to form a synthetic gas containing as main components hydrogen ($H_2$), carbon monoxide (CO) and carbon dioxide ($CO_2$).

The steam reforming reaction is an endothermic reaction. Therefore, the reformer comprises a reaction tube loaded with the catalyst and a combustion device surrounding the outer surface of the reaction tube. A fuel gas and air are supplied into the combustion device to burn the fuel gas so as to heat the inner region of the reaction tube to, for example, 700 to 900° C. As a result, a reaction heat is supplied to the reaction system so as to carry out the steam reforming reaction more effectively.

In the step of forming the synthetic gas, carbon dioxide contained in the waste combustion gases generated in the boiler for steam generation and generated in the combustion device is recovered so as to be supplied to at least one of the upstream side and downstream side of the moistening device. A chemical absorption method using an ordinary amine absorption liquid is utilized for recovering carbon dioxide from the waste combustion gas. However, the carbon dioxide recovery method is not particularly limited in the present invention, as far as carbon dioxide can be recovered efficiently.

(2) Crude Methanol Synthesizing Step

The synthetic gas is forwarded from the synthetic gas forming step 1 shown in FIG. 1 into the methanol synthesizing step 2. In this step, the heat of the synthetic gas is recovered through, for example, a waste heat boiler, the moistening device or a heat exchanger, with the result that the synthetic gas is cooled substantially to room temperature. The steam contained in the synthetic gas is condensed in accordance with temperature reduction of the synthetic gas in the heat recovery process so as to be recovered as a condensed water, which is supplied to, for example, the moistening device, the boiler, etc.

The synthetic gas cooled to room temperature is compressed by a compressor to a pressure of, for example, 50 to 150 atmospheres and, then, preheated to, for example, 200 to 300° C. The preheated synthetic gas is supplied into the reaction tube loaded with a methanol synthesizing catalyst. Reactions (1) and (2) given below are performed within the reaction tube to synthesize methanol:

  (1)

  (2)

In these reactions, impurities such as dimethyl ether and ethanol are formed by side reactions. These impurities and water are contained in a liquid crude methanol together with methanol.

For example, a copper-based catalyst is used as the methanol synthesizing catalyst. Particularly, it is desirable to use as the methanol synthesizing catalyst oxides of Cu, Zn, Al, Ga and M, which is at least one element selected from the alkaline earth metal elements and rare earth elements, said oxide exhibiting a high durability under an atmosphere containing a high concentration of carbon dioxide. The atomic ratio of these Cu. Zn, Al, Ga and M, i.e., Cu:Zn:Al:Ga:M, should desirably be 100:10 to 200:1 to 20:1 to 20:0.1 to 20.

(3) Distilling Step

The liquid crude methanol is forwarded from the methanol synthesizing step 2 to, for example, a distillation column of the distilling step 3 shown in FIG. 1 so as to be separated by distillation into a refined methanol and a liquid waste material containing by-products of low boiling point organic compounds and high boiling point organic compounds. The by-products contained in the liquid waste material are discharged to the outside of the system.

In the methanol manufacturing method of the present invention, carbon dioxide discharged from combustion devices for the boiler and the reformer is recovered and, then, compressed by a compressor to a predetermined pressure. Then, the compressed carbon dioxide is supplied to at least one fluid passageway selected from the fluid passageway positioned upstream of the moistening device and the fluid passageway interposed between the moistening device and the reformer.

Carbon dioxide generated in another factory, etc. can also be used in the present invention in addition to the carbon dioxide recovered in the methanol manufacturing process. Since carbon dioxide, which was discharged from the conventional factory, etc. to the air atmosphere, can be effectively utilized as a raw material in the methanol manufacturing method of the present invention, the amount of carbon dioxide discharged to the air atmosphere can be decreased. In other words, the method of the present invention is desirable as a measure against warming of the earth.

In the first embodiment of the present invention described above, carbon dioxide is supplied to at least one of the fluid passageway positioned upstream of the moistening device and the fluid passageway interposed between the moistening device and the reformer. Also, the raw material gas containing hydrocarbon as a main component is supplied to the moistening device for moistening the raw material gas. It follows that the amount of the moistened raw material gas is increased by an amount corresponding to the supply amount of carbon dioxide. Since the moistened raw material gas containing carbon dioxide supplied from the outside is supplied to the reformer, it is possible to decrease the amount of the superheated steam prepared in the boiler or the like and supplied separately to the moistened raw material gas. Naturally, the running cost for the methanol manufacture can be decreased.

It should be noted in particular that, since carbon dioxide is supplied together with the raw material gas to the fluid passageway positioned upstream of the moistening device, both the raw material gas and carbon dioxide are moistened while passing through the moistening device. In other words, a moistened mixed gas consisting of the raw material gas and carbon dioxide is supplied to the reformer, making it possible to further decrease the amount of the superheated steam prepared in the boiler or the like and supplied separately to the moistened raw material gas. It follows that the running cost for the methanol manufacture can be further decreased.

It should also be noted that, since carbon dioxide is supplied to at least one of the fluid passageway positioned upstream of the moistening device and the fluid passageway interposed between the moistening device and the reformer, the raw material gas containing hydrocarbon as a main component, carbon dioxide and steam can be supplied to the reformer. As a result, carbon monoxide and hydrogen can be formed in the reformer by reaction (3) given below between carbon dioxide and the raw material gas, e.g., methane gas, in addition to the synthetic gas containing hydrogen ($H_2$), carbon monoxide (CO) and carbon dioxide ($CO_2$):

$$CO_2 + CH_4 \rightarrow 2CO + 2H_2 \quad (3)$$

Clearly, the amount of carbon dioxide contained in the synthetic gas formed in the reformer can be decreased, compared with the conventional case where carbon dioxide is supplied to the synthetic gas formed in the reformer. As a result, a synthetic gas lower in the carbon dioxide content can be supplied from the reformer to the methanol synthesizing step, making it possible to prevent the methanol synthesizing catalyst used in the methanol synthesizing step from being exposed to an atmosphere having a high carbon dioxide concentration. It follows that the activity of the methanol synthesizing catalyst is prevented from being lowered.

Further, carbon dioxide recovered from the waste combustion gases generated from the boiler and the combustion device of the reformer can be supplied to at least one of the fluid passageway positioned upstream of the moistening device and the fluid passageway interposed between the moistening device and the reformer so as to decrease the amount of carbon dioxide discharged to the outside during the methanol manufacturing process. It follows that the methanol manufacturing plant is rendered advantageous in economy where a tax and regulation for the carbon dioxide discharge are started in future.

EXAMPLE 1

The methanol manufacture according to the first embodiment of the present invention will now be described more in detail as Example 1 with reference to the methanol manufacturing plant shown in FIG. 2.

Figure 2:
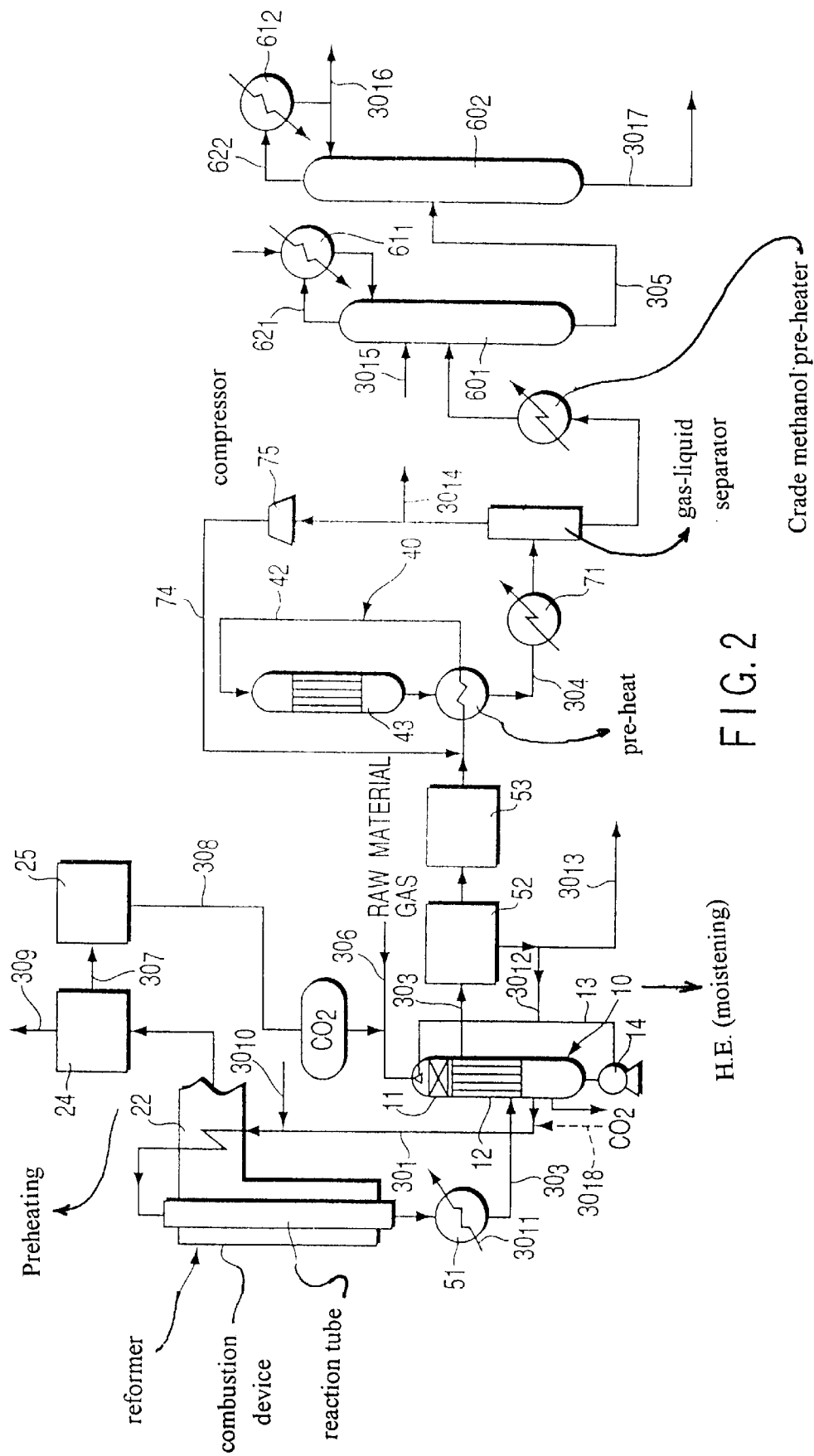
FIG. 2 schematically shows the construction of the methanol manufacturing plant used in Example 1 of the present invention.

Specifically, the plant shown in FIG. 2 comprises a single stage heat exchange type moistening device 10. Arranged within the moistening device 10 are a loading layer 11 positioned in an upper portion of the moistening device 10 and a tube 12 positioned below the loading layer 11 for bringing a gas into contact with water by a wet wall system. A pump 14 for circulating water from the bottom portion of the moistening device 10 toward the top of the moistening device 10 through a circulating water passageway 13 is arranged below the moistening device 10.

A reformer 20, which is arranged downstream of the moistening device 10, is connected to the moistening device 10 via a fluid passageway $30_1$. The reformer 20 comprises a steam reforming reaction tube 21 and a combustion device 23 arranged to surround the reaction tube 21 and equipped with a preheating section 22. A steam reforming catalyst, e.g., a nickel-based catalyst, is loaded in the reaction tube 21. The fluid passageway $30_1$ extends through the preheating section 22 so as to be connected to the reaction tube 21. Further, a carbon dioxide recovery device 24 is connected via a fluid passageway $30_2$ to the preheating section 22.

A reaction apparatus 40 for synthesizing methanol is arranged downstream of the reformer 20 and connected to the reformer 20 via a fluid passageway $30_3$. The reaction apparatus 40 comprises a pre-heater 41 and a reactor 43 for synthesizing methanol. The synthetic gas coming from the pre-heater 41 is supplied to the reactor 43 through a circulating fluid passageway 42. Loaded in the reactor 43 is a methanol synthesizing catalyst consisting of oxides of Cu, Zn, Al, Ga and M, which is at least one element selected from the alkaline earth metal elements and the rare earth elements, these Cu, Zn, Al, Ga and M being mixed at an atomic ratio of 100:10 to 200:1 to 20:1 to 20:0.1 to 20. Mounted to the fluid passageway $30_3$ interposed between the reformer 20 and the pre-heater 41 are a heat exchanger 51, a heat recovery device 52 and a first compressor 53 in the order mentioned as viewed from the reformer 20. That portion of the fluid passageway $30_3$ which is interposed between the heat exchanger 51 and the heat recovery device 52 extends through the tube 12 included in the moistening device 10.

A first distillation column $60_1$ is arranged downstream of the reaction apparatus 40 for synthesizing methanol and connected to the reaction apparatus 40 via a fluid passageway $30_4$ arranged downstream of the reaction apparatus 40. A first condenser $61_1$ is connected to a top portion of the first distillation column $60_1$ via a circulating fluid passageway $62_1$. One end of the fluid passageway $30_4$ referred to previously is connected to a bottom portion of the reactor 43. Mounted to that portion of the fluid passageway $30_4$ which is interposed between the reactor 43 of the reaction apparatus 40 for synthesizing methanol and the first distillation column $60_1$ are the pre-heater 41, a cooling device 71, a gas-liquid separator 72 and a crude methanol pre-heater 73 in the order mentioned as viewed from the reactor 43. The gas-liquid separator 72 is connected to the fluid passageway $30_3$ at the inlet of the pre-heater 41 via a gas circulating passageway 74 having a gas compressor 75 mounted thereto.

A second distillation column $60_2$ is arranged downstream of the first distillation column $60_1$ and connected to the first distillation column $60_1$ through a fluid passageway $30_5$. A second condenser $61_2$ is connected to a top portion of the second distillation column $60_2$ through a circulating fluid passageway $62_2$.

Figure 3:
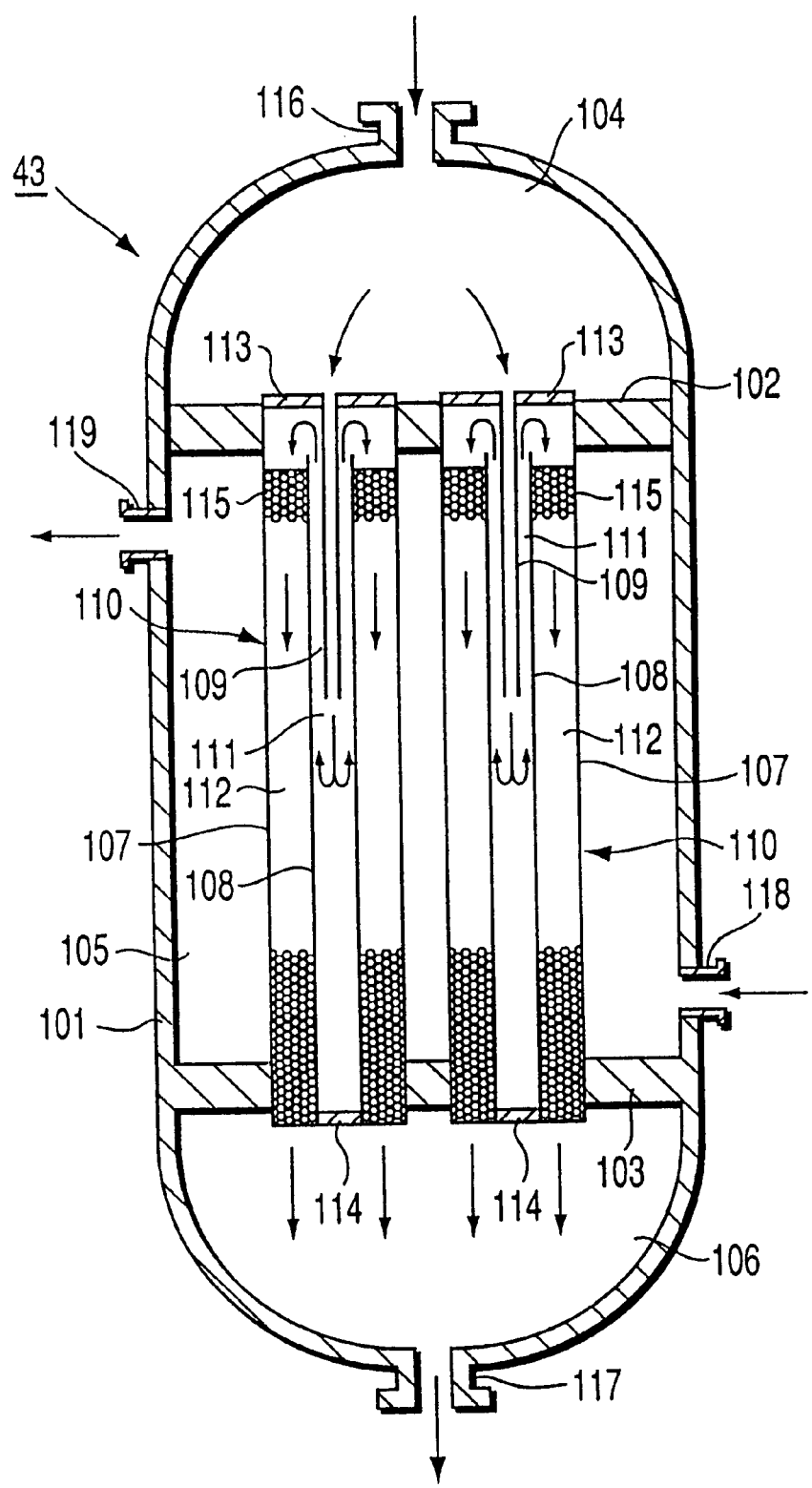
FIG. 3 is a cross sectional view showing as an example a reaction apparatus for synthesizing methanol, said reaction apparatus being incorporated in the plant shown in FIG. 2.

It is desirable for the reactor 43 for synthesizing methanol to include a triple tube as shown in, for example, FIG. 3. As shown in FIG. 3, the reactor 43 includes a reactor body 101 that is partitioned by two partition plates 102 and 103 into three chambers consisting of a synthetic gas supply chamber 104 positioned in the upper portion of the reactor body 101, a cooling medium circulating chamber 105 positioned below the synthetic gas supply chamber 104, and a methanol-containing gas residence chamber 106 positioned in the lower portion of the reactor body 101. A plurality of triple tubes 110, e.g., two triple tubes, each consisting of an outer tube 107, an intermediate tube 108 and an inner tube 109 extend through the two partition plates 102 and 103 so as to be supported by these partition plates 102 and 103. An inner annular space 111 is formed between the inner tube 109 and the intermediate tube 108, and an outer annular space 112 is formed between the intermediate tube 108 and the outer tube 107. The upper end of the intermediate tube 108 is positioned lower than the upper end of the outer tube 107. The lower end of the inner tube 109 is positioned in a central portion of the intermediate tube 108. It is important to determine appropriately the lower end of the inner tube 109. Specifically, the distance of the lower end of the inner tube 109 from the upper end of the triple tube 111 should desirably be 1/10 to 2/3 of the entire length of the triple tube 111 in order to suppress the pressure loss and to obtain the cooling effect of the catalyst from the inside, which will be described hereinlater.

The upper end of the triple tube 110 is closed by an upper shielding plate 113 such that the inner tube 109 alone is left open. On the other hand, the lower end of the triple tube 110 is closed by a lower shielding plate 114 such that the intermediate tube 108 is closed and the outer annular space 112 is left open. A catalyst layer 115 consisting of, for example, a granular methanol synthesizing catalyst is loaded in the outer annular space 112 formed between the intermediate tube 108 and the outer tube 107. The catalyst layer 115 extends from the bottom of the outer annular space 112 to reach a region near the upper end of the annular space 112. A mesh plate or a porous plate (not shown) is mounted to the lower end of the outer annular space 112 in order to prevent the granular methanol synthesizing catalyst from falling down.

A supply port 116 for supplying the synthetic gas into the synthetic gas supply chamber 104 is formed in an upper portion of the reactor body 101. The circulating fluid passageway 42 referred to previously is connected to the supply port 116. Also, a discharge port 117 for discharging the methanol-containing gas formed in the triple tube 110 is formed in a lower portion of the reactor body 101. The fluid passageway $30_4$ referred to previously is connected to the discharge port 117. Further, an inlet port 118 and an outlet port 119 for a cooling medium are formed through the side wall of the cooling medium circulating chamber 105 of the reactor body 101.

Methanol is manufactured by utilizing the methanol manufacturing plant shown in FIG. 2 as follows.

Specifically, the raw material gas containing hydrocarbon as a main component, which has already been desulfurized and preheated, is supplied to the loading layer 11 at the top of the heat exchanger type moistening device 10 through a fluid passageway $30_6$. At the same time, carbon dioxide recovered in the carbon dioxide recovery device 24 is introduced into the compressor 25 through a fluid passageway $30_7$ so as to be compressed to have a higher pressure. The compressed carbon dioxide is supplied to the fluid passageway $30_6$ so as to be mixed with the raw material gas, with the result that the mixed gas is supplied from the fluid passageway $30_6$ into the loading layer 11 at the top of the moistening device 10. The pump 14 arranged below the moistening device 10 is operated in advance to permit water to be circulated from the bottom portion of the moistening device 10 to the top portion of the moistening device 10 via the circulating water passageway 13. As a result, the mixed gas of the raw material gas and carbon dioxide supplied to the top portion of the moistening device 10 is moistened by the circulating water. To be more specific, the mixed gas is brought into contact with the water supplied from the circulating water passageway 13 in the loading layer 11 so as to be moistened and, then, exchanges heat with the synthetic gas of a high temperature supplied from the reformer 20 through the fluid passageway $30_3$ so as to be heated and further moistened. Incidentally, the gas after carbon dioxide recovery in the carbon dioxide recovery device 24 is discharged to the air atmosphere through a fluid passageway $30_9$.

The moistened mixed gas is supplied into the steam reforming reaction tube 21 of the reformer 20 through the fluid passageway $30_1$. A required amount of a process steam is added through a fluid passageway $30_{10}$ to the moistened mixed gas flowing within the fluid passageway $30_1$ and, then, the mixed gas is supplied to the reaction tube 21 through the preheating section 22 positioned in the convection section of the reformer 20. The raw material gas containing hydrocarbon as a main component, steam and carbon dioxide are supplied to the reaction tube 21 of the reformer 20. Within the reaction tube 21, hydrocarbon, e.g., methane, is subjected to steam reformation in the presence of the catalyst loaded in the reaction tube 21 to form a synthetic gas containing carbon monoxide, carbon dioxide and hydrogen. At the same time, reaction between carbon dioxide and methane is carried out to form a synthetic gas containing carbon monoxide and hydrogen.

Since the reforming reaction is an endothermic reaction, a mixture of a fuel gas and the air is burned within the combustion device 23 of the reformer 20 so as to heat the inner space of the reaction tube 21 to, for example, 800 to 1,000° C. The combustion waste gas is supplied to the carbon dioxide recovery device 24 through the preheating section 22 and the fluid passageway $30_2$ for recovery of carbon dioxide. Carbon dioxide thus recovered is supplied to the moistening device 10 as described previously.

The synthetic gas formed in the reformer 20 is supplied to the heat exchanger 51 through the fluid passageway $30_3$ and exchanges heat with a boiler water circulating through a fluid passageway $30_{11}$ to generate steam of a high pressure. Then, the synthetic gas is supplied to an outside fluid passageway of the tube 12 of the moistening device 10. The heat of the synthetic gas is partly recovered in the moistening device 10 so as to be utilized as a heat source of the moistening device 10.

The synthetic gas coming from the tube 12 is supplied to the heat recovery device 52 so as to be cooled to room temperature. In this step, the steam contained in the synthetic gas is condensed, and the condensed water is partly supplied to the circulating water passageway 13 of the moistening device 10 through a fluid passageway $30_{12}$ so as to be utilized for the moistening of the mixed gas of the raw material gas and carbon dioxide introduced into the moistening device 10. The remaining condensed water flows through a fluid passageway $30_{13}$ so as to be utilized as, for example, a process water.

The synthetic gas from which the condensed water has been separated is supplied to the first compressor 53 through the fluid passageway $30_3$ so as to be compressed to a pressure adapted for the methanol synthesizing reaction, e.g., to a pressure of 50 to 150 atmospheres. The compressed synthetic gas having a high pressure is supplied to the pre-heater 41 of the reaction apparatus 40 for synthesizing methanol through the fluid passageway $30_3$ so as to be preheated to a temperature adapted for the methanol synthesizing reaction, e.g., 200 to 300° C. Further, the preheated synthetic gas is supplied through the circulating passageway 42 to the reactor 43 having the methanol synthesizing catalyst loaded therein. Incidentally, the unreacted gas separated in the gas-liquid separator 72 is supplied to that portion of the fluid passageway $30_3$ which is positioned upstream of the pre-heater 41 so as to be mixed with the synthetic gas. In the reactor 43, the reactions (1) and (2) given previously are carried out to synthesize methanol. It is desirable to use a reactor housing the triple tube shown in FIG. 3 as the reactor 43.

To be more specific, the synthetic gas is supplied through the supply port 116 into the synthetic gas supply chamber 104 of the reactor body 101. The synthetic gas within the supply chamber 104 flows downward through the upper end of the inner tube 109 of the triple tube 110 into the inner tube 109 and, then, further flows through the outlet port at the lower end of the inner tube 109 into the inner annular space 111 formed between the inner tube 109 ad the intermediate tube 108. The synthetic gas further flows upward through the inner annular space 111 to flow into an outer annular space 112 formed between the intermediate tube 108 and the outer tube 107 through the upper end of the outer annular space 112. Still further, the synthetic gas flows downward through the catalyst layer 115 loaded in the outer annular space 112. While the synthetic gas flows through the catalyst layer 115, the reactions (1) and (2) given previously are carried out to synthesize methanol.

During the methanol synthesis described above, a cooling medium such as a boiler water is supplied through the inlet port 118 of the cooling medium into the cooling medium circulating chamber 105 of the reactor body 101 and is discharged to the outside through the cooling medium outlet port 119 so as to cool the catalyst layer 115 through the outer tube 107. It should also be noted that the reacting section for performing the methanol synthesizing reaction is formed by the triple tube in the first embodiment of the present invention. Specifically, the synthetic gas is allowed to flow into the catalyst layer loaded in the outer annular space 112 through the inner tube 109 and the inner annular space 111. It follows that the catalyst layer is cooled from the inside by the synthetic gas so as to suppress effectively the heat generation accompanying the methanol synthesizing reaction and, thus, to suppress effectively the deactivation of the catalyst caused by the heat generation.

It should be noted in particular that carbon dioxide is supplied to the reformer 20 and a synthetic gas having relatively high concentrations of carbon monoxide is utilized in the present invention. In this case, the rate of the methanol synthesizing reaction is increased so as to increase the heat generation rate and, thus, to increase the catalyst temperature. As a result, the activity of the catalyst is likely to be lowered. In the present invention, however, the triple tube 110 is housed in the reactor 43, and the catalyst layer 115, in which the temperature is rapidly increased by the exothermic reaction of the synthetic gas, is cooled by the cooling medium and the synthetic gas so as to maintain a high catalytic activity over a long period of time.

Even if a synthetic gas having relatively high concentrations of carbon monoxide is utilized, the heat generating rate in the methanol synthesizing step can be suppressed by circulating the unreacted gas into the synthetic gas so as to decrease concentrations of carbon monoxide in the synthetic gas.

In the next step, the reaction gas mixture formed in the reactor 43 is supplied through the fluid passageway $30_4$ into each of the pre-heater 41 and the cooling device 71, as shown in FIG. 2 so as to cool the reaction gas mixture to substantially room temperature. In this step, almost all methanol and water within the reaction gas mixture are condensed so as to flow as a liquid stream into the gas-liquid separator 72. In this separator 72, the liquid crude methanol is separated from the unreacted gas.

The unreacted gas is forwarded into the gas compressor 75 through the gas circulating passageway 74 so as to be compressed to have a high pressure. The compressed gas is circulated into the fluid passageway $30_3$ at the inlet of the pre-heater 41 so as to be supplied into the reactor 43 together with the synthetic gas. The unreacted gas is partly supplied through a fluid passageway $30_{14}$ as a purge gas so as to be utilized as a fuel for the reformer 20.

On the other hand, the crude methanol is supplied into the first distillation column $60_1$ through the crude methanol pre-heater 73 mounted to the fluid passageway $30_4$. A small amount of water is supplied as required to the first distillation column $60_1$ through a fluid passageway $30_{15}$. The low boiling point organic compounds are concentrated at the top portion of the first distillation column $60_1$ and are partly condensed in the first condenser $61_1$, with the remainder being discharged to the outside of the system together with the dissolved gas. The bottom fraction of the first distillation column $60_1$, which consists mainly of methanol and water, is supplied to the second distillation column $60_2$ through the fluid passageway $30_5$.

The methanol fraction is cooled and condensed by the second condenser $61_2$ so as to be refined into methanol of a high purity by reflux. The high purity methanol is withdrawn as a product methanol from the top portion of the second distillation column $60_2$ to the outside through a fluid passageway $30_{16}$. The bottom fraction of the second distillation column $60_2$, which constitutes a waste water, mainly contains water, and also contains small amounts of high boiling point organic compounds and organic acids and traces of inorganic materials coming from the apparatus. The waste water is discharged from the bottom portion of the second distillation column $60_2$ to the outside of the system through a fluid passageway $30_{17}$.

In Example 1 described above, the waste combustion gas discharged from the combustion device 23 of the reformer 20 is introduced into the carbon dioxide recovery device 24, and the recovered carbon dioxide is compressed by the compressor 25 so as to be compressed to have a high pressure. The compressed carbon dioxide is supplied to the fluid passageway $30_6$ upstream of the moistening device 10 so as to be mixed with the raw material gas supplied to the fluid passageway $30_6$. Then, the mixed gas is supplied to the top portion of the moistening device 10. Naturally, the flow rate of the gas supplied to the moistening device 10 is increased, compared with the case where carbon dioxide is not added to the raw material gas, leading to an increased moistening rate in the moistening device 10. It follows that it is possible to decrease the amount of the process steam supplied from the fluid passageway $30_{10}$.

For example, if carbon dioxide is added in an amount of about 30% of the raw material gas flow rate, the moistened amount can also be increased by about 30%. The amount of the process steam can be decreased in an amount corresponding to the increase in the moistened amount.

It should also be noted that carbon dioxide recovered from the combustion waste gas discharged from the combustion device 23 of the reformer 20 (and/or from the boiler for steam generation) is utilized as the carbon dioxide gas supplied to the fluid passageway $30_6$ upstream of the moistening device 10 so as to decrease the amount of carbon dioxide discharged from the methanol manufacturing plant. As a result, the methanol manufacturing plant is rendered advantageous in economy when a tax and regulation of the carbon dioxide discharge are started in future.

What should also be noted is that the methanol synthesizing catalyst used in the present invention consists of oxides of Cu, Zn, Al, Ga and M, which is at least one element selected from the alkaline earth metal elements and the rare earth elements, these Cu, Zn, Al, Ga and M being mixed at an atomic ratio of 100:10 to 200:1 to 20:1 to 20:0.1 to 20. The catalyst of the particular composition exhibits a high durability when exposed to a synthetic gas containing a high concentration of carbon dioxide gas. In other words, deterioration of the catalytic activity is suppressed, making it possible to decrease the amount of the catalyst used.

Also, the methanol synthesizing reactor 43 housing the triple tube 110 shown in FIG. 3 is used in Example 1 of the present invention, making it possible to lower the synthetic gas temperature at the inlet to the catalyst layer. As a result, it is possible to decrease the amount of the unreacted gas separated in the gas-liquid separator 72 and circulated for lowering the carbon monoxide concentration in the synthetic gas to the fluid passageway $30_3$ through which flows the synthetic gas, leading to saving of the circulating power.

In Example 1 described above, carbon dioxide recovered from the combustion device 23 of the reformer 20 is compressed and, then, supplied to the fluid passageway $30_8$ upstream of the moistening device. Alternatively, however, it is also possible to supply carbon dioxide to the fluid passageway $30_1$ positioned downstream of the moistening device 10 through the fluid passageway $30_{18}$ as shown in FIG. 2 so as to decrease the amount of the process steam as in Example 1.

(Second Embodiment)

In the flow chart for the methanol manufacture shown in FIG. 1, the moistening device comprises a first stage moistening device and a second stage moistening device arranged intermediate between the first stage moistening device and the reformer. The waste water recovered in the distilling step is supplied to the circulating water passageway for the first stage moistening device. Also, a mixed gas consisting of the raw material gas containing hydrocarbon as a main component and carbon dioxide is supplied from upstream side of the first stage moistening device to the top portion of the first stage moistening device.

It is possible to supply an additional carbon dioxide stream to at least one fluid passageway selected from the group consisting of the fluid passageway connecting the first stage and second stage moistening devices and the fluid passageway interposed between the second stage moistening device and the reformer.

In the second embodiment outlined above, the presence of the first stage and second stage moistening devices makes it possible to supply a sufficiently moistened mixed gas to the reformer so as to decrease the amount of the process steam, compared with the first embodiment described previously.

In the second embodiment, a mixed gas consisting of the raw material gas and carbon dioxide is supplied to the top portion of the first stage moistening device. Therefore, the mixed gas is brought into contact with water supplied from the circulating water passageway to the loading layer at the top portion of the first stage moistening device so as to be moistened. In this step, the waste water recovered from the distilling step is supplied to the circulating water passageway so as to allow carbon dioxide contained in the mixed gas to neutralize the salts of alkali metals and alkaline earth metals contained in the waste water. As a result, the pH value of the waste water is shifted from the alkaline side toward the neutral or acidic side. It follows that, even if the waste water recovered from the distilling step is supplied to the circulating water passageway of the first stage moistening device, the first stage moistening device is prevented from being corroded by the alkali, making it possible to effectively utilize the waste water.

EXAMPLE 2

In Example 2, the methanol manufacture according to the second embodiment of the present invention will be specifically described with reference to the gist portion of the methanol manufacturing plant shown in FIG. 4. Incidentally, the reference numerals commonly used in FIGS. 2 and 4 represent the same members of the plant and, thus, explanation thereof will be omitted in the following description.

Figure 4:
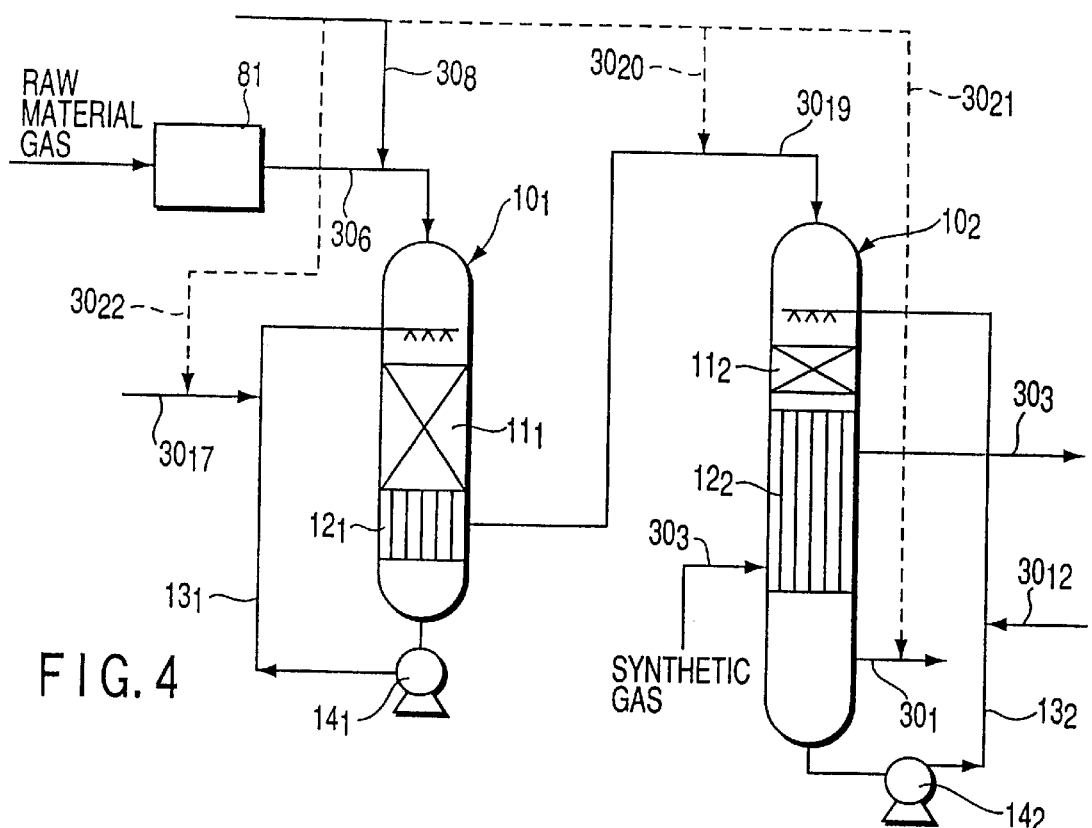
FIG. 4 schematically shows a gist portion of the methanol manufacturing plant used in Example 2 of the present invention.

A reference numeral $10_1$ shown in FIG. 4 represents a single stage type first stage moistening device. A loading layer $11_1$ extending vertically downward from the top portion and a tube $12_1$ positioned below the loading layer $11_1$ for bringing the gas into contact with water by wet wall system are arranged within the first stage moistening device $10_1$. A first pump $14_1$ for circulating water from the bottom portion of the first stage moistening device to the top portion of the moistening device $10_1$ through a first circulating water passageway $13_1$ is arranged below the moistening device $10_1$. The waste water discharged from the second distillation column is supplied to the first circulating water passageway $13_1$ through the fluid passageway $30_{17}$.

A single stage heat exchange type second moistening device $10_2$ is arranged downstream of the first stage moistening device $10_1$ and connected to the first stage moistening device $10_1$ via the fluid passageway $30_{19}$. Arranged within the second stage moistening device $10_2$ are a loading layer $11_2$ extending downward from the top portion of the moistening device $10_2$ and a tube $12_2$ positioned below the loading layer $11_2$ for bringing the gas into contact with water by a wet wall system. One end of the fluid passageway $30_{19}$ is connected to the side wall of the first stage moistening device, with the other end connected to the top portion of the second stage moistening device $10_2$. A second pump $14_2$ for circulating water from the bottom portion of the second stage moistening device $10_2$ to the top portion of the second stage moistening device $10_2$ via a second circulating water passageway $13_2$ is arranged below the second stage moistening device $10_2$. The second stage moistening device $10_2$ is connected the reformer arranged downstream of the second stage moistening device $10_2$ via the fluid passageway $30_1$. Also, the synthetic gas generated from the reformer is introduced into the tube $12_2$ of the second stage moistening device $10_2$ through the fluid passageway $30_3$ so as to carry out heat exchange.

In the methanol manufacturing plant shown in FIG. 4, the raw material gas containing hydrocarbon as a main component is desulfurized in a desulfurizing apparatus 81 and preheated as in Example 1 and, then, supplied toward the loading layer $11_1$ in the top portion of the single stage type first stage moistening device $10_1$ through the fluid passageway $30_6$. At the same time, carbon dioxide recovered in, for example, a carbon dioxide recovery device and compressed by a compressor is supplied to the fluid passageway $30_6$ through the fluid passageway $30_8$. It follows that a mixed gas consisting of carbon dioxide and the raw material gas is supplied through the fluid passageway $30_6$ into the loading layer $11_1$ in the top portion of the first stage moistening device $10_1$. It should be noted that the first pump $14_1$ arranged below the moistening device $10_1$ is operated in advance so as to circulate water from the bottom portion of the moistening device $10_1$ to the top portion of the moistening device $10_1$ via the first circulating water passageway $13_1$ and, at the same time, the waste water discharged from the second distillation column is supplied to the first circulating water passageway $13_1$ through the fluid passageway $30_{17}$. Because of the water circulation, the mixed gas supplied to the top portion of the first stage moistening device $10_1$ is brought into contact within the loading layer $11_1$ with the water supplied from the first circulating water passageway $13_1$, and then brought into contact within the tube $12_1$ with the water so as to be moistened. In this step, salts of the alkali metals and alkaline earth metals contained in the waste water supplied to the first circulating water passageway $13_1$ are neutralized by carbon dioxide contained in the mixed gas. Therefore, even if the waste water recovered in the distilling step is supplied to the first circulating water passageway $13_1$, the first stage moistening device $10_1$ is prevented from being corroded by the alkali.

The mixed gas moistened in the first stage moistening device $10_1$ is supplied to the loading layer $11_2$ at the top portion of the second stage moistening device $10_2$ through the fluid passageway $30_{19}$. It should be noted that the second pump $14_2$ arranged below the second stage moistening device $10_2$ is operated in advance so as to circulate water from the bottom portion of the second stage moistening device $10_2$ to the top portion of the second stage moistening device $10_2$ through the second circulating water passageway $13_2$ so as to moisten the mixed gas supplied to the top portion of the moistening device $10_2$. In other words, the mixed gas is brought into contact within the loading layer $11_2$ with the water supplied from the second circulating water passageway $13_2$ so as to be moistened. Then, the moistened mixed gas exchanges heat within the tube $12_2$ with the synthetic gas of a high temperature supplied from the reformer through the fluid passageway $30_3$ so as to be heated. Incidentally, it is possible to supply the condensed water discharged from the heat recovery device to the second circulating water passageway $13_2$ through the fluid passageway $30_{12}$ as already described in conjunction with Example 1.

The mixed gas moistened in the second stage moistening device $10_2$ is supplied to the reformer through the fluid passageway $30_1$ so as to be utilized for the synthetic gas formation and methanol synthesis as in Example 1. Finally, a refined methanol is recovered from the distillation column.

Of course, the effect similar to that obtained in Example 1 can be obtained in Example 2. In addition, the use of the first stage and second stage moistening devices $10_1$ and $10_2$ makes it possible to supply a sufficiently moistened mixed gas to the reformer, with the result that the amount of the process steam used can be decreased, compared with Example 1.

Also, carbon dioxide is supplied to a fluid passageway positioned upstream of the first stage moistening device $10_1$ in Example 2. Therefore, even if the waste water discharged from the distilling step and containing salts of alkali metals or alkaline earth metals is supplied to the first circulating water passageway $13_1$, the pH value of the waste water is shifted toward the neutral side and, further, toward the acidic side so as to prevent the first moistening device $10_1$ from being corroded by the alkali. It follows that the waste water can be utilized effectively.

In Example 2, carbon dioxide is supplied to the fluid passageway positioned upstream of the first stage moistening device $10_1$. Alternatively, it is also possible to supply carbon dioxide to the fluid passageway $30_{19}$ connecting the first stage and second stage moistening devices $10_1$ and $10_2$ through the fluid passageway $30_{20}$ or to the fluid passageway $30_1$, through which the mixed gas is supplied to the reformer, through the fluid passageway $30_{21}$ as shown in FIG. 4. Further, it is possible to supply carbon dioxide directly to the fluid passageway $30_{17}$ for the waste water from the distillation column.

Since carbon dioxide can be supplied to several specified points in addition to the fluid passageway positioned upstream of the first moistening device $10_1$, the flow rate of the mixed gas to be moistened can be increased so as to further decrease the amount of the process steam used, compared with Example 1.

(Third Embodiment)

Figure 5:
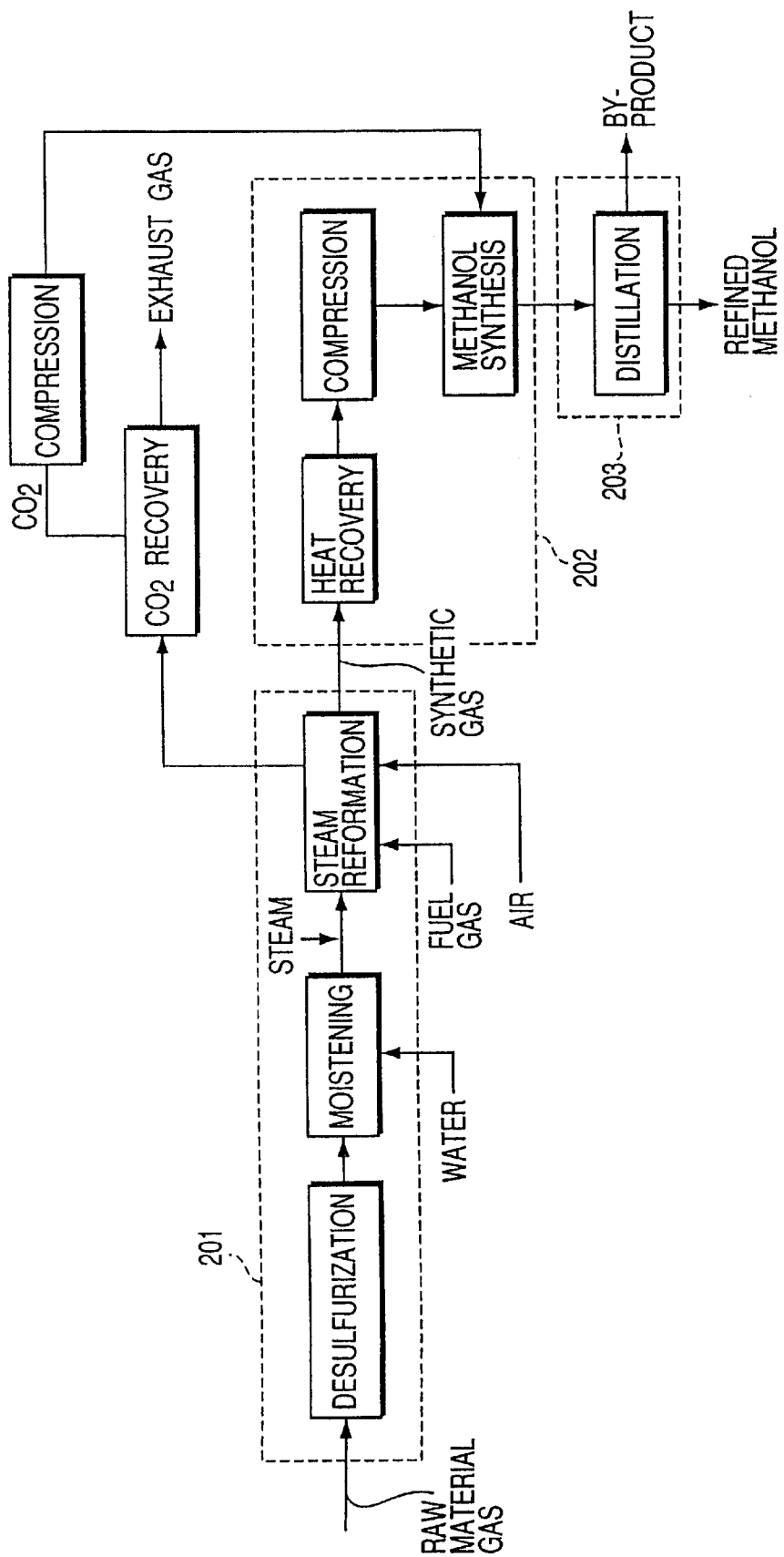
FIG. 5 is a flow chart showing a methanol manufacturing process according to another embodiment of the present invention.

FIG. 5 is a flow chart showing the methanol manufacturing process employed in the third embodiment of the present invention.

The methanol manufacturing process shown in FIG. 5 comprises a synthetic gas forming step 201, a methanol synthesizing step 202 and a distillation step 203.

(1) Synthetic Gas Forming Step

The raw material gas containing hydrocarbon as a main component, e.g., a natural gas, is supplied to a desulfurization device so as to remove traces of sulfur compounds contained in the raw material gas. The raw material gas after the desulfurization is introduced into a moistening device in which steam of, for example, 150 to 250° C. is added in a saturated pressure to the raw material gas.

The moistened raw material gas is mixed with a superheated steam prepared in, for example, a boiler and, then, introduced into a reformer. It is desirable for the amount of the steam contained in the gas introduced into the reformer to be about 2 to 3 times as large as the volume flow rate of the raw material gas.

The raw material gas introduced into the reformer is reformed by the steam introduced into the reformer at 800 to 1,000° C. together with the raw material gas in the presence of, for example, a nickel-based catalyst so as to form a synthetic gas containing mainly hydrogen ($H_2$), carbon monoxide (CO) and carbon dioxide ($CO_2$). The synthetic gas has a hydrogen concentration higher than that required for hydrogen to react with carbon monoxide to form methanol.

The steam reforming reaction is an endothermic reaction. Therefore, the reformer comprises a reaction tube loaded with a catalyst and a combustion device surrounding the outer surface of the reaction tube. A fuel gas and the air are introduced into the combustion device to burn the fuel so as to heat the inner space of the reaction tube to, for example, 700 to 900° C. By supplying the reaction heat in this fashion, the steam reforming reaction is carried out efficiently.

In the synthetic gas forming step, carbon dioxide is recovered from the combustion waste gas generated in the boiler for steam generation and from the combustion gas generated in the combustion device. The carbon dioxide thus recovered is utilized in a second reaction step of the methanol synthesizing process described hereinlater. A chemical absorption method using in general an amine absorption liquid is employed for recovery of carbon dioxide from the waste combustion gas. However, the carbon dioxide recovery method is not particularly limited in the present invention, as far as carbon dioxide can be recovered efficiently.

(2) Crude Methanol Synthesizing Step

The synthetic gas is forwarded from the synthetic gas forming step 201 shown in FIG. 5 to the methanol synthesizing step 202. In this step, the heat of the synthetic gas is recovered by, for example, a waste heat boiler, a moistening device or a heat exchanger, with the result that the synthetic gas is cooled to substantially room temperature. The steam contained in the synthetic gas is condensed in accordance with the temperature drop of the synthetic gas in the heat recovery process, and the condensed water is recovered for use as a moistening water in the moistening device and as water supplied to the boiler.

The synthetic gas cooled to room temperature is compressed by a compressor to have a pressure of 50 to 150 atmospheres and, then, preheated to, for example, 200 to 300° C. The preheated synthetic gas is supplied to the reactor loaded with a methanol synthesizing catalyst. Reactions (1) and (2) described previously are carried out in the reactor to synthesize methanol. In this step, the hydrogen concentration is higher than that required for hydrogen to react with carbon monoxide to manufacture methanol. In other words, by using a hydrogen-rich synthetic gas, the rate of heat generation accompanying the methanol synthesizing reaction is moderated so as to suppress deactivation of the catalyst.

It should be noted that impurities such as dimethyl ether and ethanol are formed by side reactions. These impurities and water are contained in the crude methanol together with the synthesized methanol.

The methanol synthesizing catalyst consists of, for example, a copper-based catalyst. Particularly, it is desirable to use a methanol synthesizing catalyst exhibiting a high durability under an atmosphere containing a high concentration of carbon dioxide. To be more specific, it is desirable for the methanol synthesizing catalyst to consist of oxides of Cu, Zn, Al, Ga and M, which is at least one element selected from the alkaline earth metal elements and the rare earth elements, these Cu, Zn, Al, Ga and M being mixed at an atomic ratio of 100:10 to 200:1 to 20:1 to 20:0.1 to 20.

(3) Distilling Step

The liquid crude methanol is forwarded from the methanol synthesizing step 202 shown in FIG. 5 to, for example, a distillation column of the distilling step 203. The liquid crude methanol is distilled in the distillation column so as to be separated into a refined methanol and the waste water containing low boiling point organic compounds and high boiling point organic compounds formed as by-products. The by-products contained in the waste water are discharged to the outside of the system.

In the methanol manufacturing process of the present invention, the methanol synthesizing step is performed in a first reaction step and a second reaction step. Specifically, in the first reaction step, the synthetic gas supplied through the synthetic gas supply passageway is subjected to reaction in the presence of a methanol synthesizing catalyst, and the formed liquid crude methanol containing the unreacted gas is subjected to a gas-liquid separation. The liquid crude methanol obtained by the gas-liquid separation is recovered. On the other hand, the unreacted gas is compressed and, then, circulated to the synthetic gas supply passageway. At the same time, the unreacted gas is partly mixed with carbon dioxide and, as required, with carbon dioxide compressed to have a high pressure. The mixture is introduced into the second reaction step so as to be subjected to reaction in the presence of a methanol synthesizing catalyst, thereby forming a liquid crude methanol.

It is possible for carbon dioxide to be supplied to the inlet of the first reaction step. The carbon dioxide recovered during the methanol manufacturing process, e.g., recovered from the combustion gases discharged from the boiler or from the combustion device of the reformer, can be used in the present invention. It is also possible to use carbon dioxide discharged as a waste material from another factory, etc. What should be noted is that carbon dioxide discharged as a waste material from another factory, etc. can be effectively utilized in the present invention as a raw material in the manufacture of methanol so as to decrease the amount of carbon dioxide discharged to the air atmosphere, which is an effective measure against warming of the earth.

According to the third embodiment of the present invention described above, the methanol synthesizing process comprises the first and second reaction steps. In other words, the methanol yield can be increased by simply adding the second reaction step without markedly modifying the facilities for the methanol manufacture.

To be more specific, a hydrogen-rich synthetic gas having a hydrogen concentration higher than that required for the reaction between hydrogen and carbon monoxide to synthesize methanol is supplied to the first reaction step through the synthetic gas supply passageway so as to be subjected to the reaction to synthesize methanol in the presence of a methanol synthesizing catalyst. As a result, a liquid crude methanol containing the unreacted gas is formed while suppressing the heat generation accompanying the methanol synthesizing reaction and while suppressing the deactivation of the catalyst. Then, the liquid crude methanol containing the unreacted gas is subjected to a gas-liquid separation so as to recover the liquid crude methanol free from the unreacted gas.

As described above, the unreacted gas has a hydrogen concentration higher than that required for hydrogen to react with carbon monoxide to synthesize methanol. Therefore, the unreacted gas is compressed and, then, circulated to the synthetic gas supply passageway and, at the same time, the compressed unreacted gas is partly mixed with carbon dioxide, the mixture being introduced into the second reaction step. Therefore, reaction is carried out between hydrogen contained in the unreacted gas and carbon dioxide supplied to the second reaction step in the presence of the methanol synthesizing catalyst. It follows that a crude methanol can also be formed in the second reaction step, making it possible to effectively utilize hydrogen contained in the unreacted gas and, thus, to increase the methanol yield.

It should also be noted that the synthetic gas is diluted by the unreacted gas circulated to the synthetic gas. As a result, the heat generation rate in the step of the methanol synthesis is moderated so as to suppress deactivation of the methanol synthesizing catalyst.

Further, carbon dioxide recovered from the waste combustion gas discharged from the boiler or the combustion device of the reformer can be supplied to the second reaction step together with the unreacted gas so as to decrease the amount of carbon dioxide discharged from the methanol manufacturing plant. As a result, the methanol manufacturing plant is rendered advantageous in economy when a tax or regulation of the carbon dioxide discharge are enforced in future.

EXAMPLE 3

In Example 3, a methanol manufacture according to a third embodiment of the present invention will be described specifically with reference to a methanol manufacturing plant shown in FIG. 6.

As shown in the drawing, the methanol manufacturing plant comprises a singe stage heat exchange type moistening device 210. Housed in the moistening device 210 are a loading layer 211 extending downward from the top portion of the moistening device 210 and a tube 212 arranged below the loading layer 211 for bringing the gas into contact with water by a wet wall system. A pump 214 for circulating water from the bottom portion of the moistening device 210 to the top portion of the moistening device 210 via a circulating water passageway 213 is arranged below the moistening device 210.

A reformer 220 is arranged downstream of the moistening device 210 and connected to the moistening device 210 via a fluid passageway 230$_1$. The reformer 220 comprises a steam reforming reaction tube 221 and a combustion device 223 arranged to surround the outer surface of the reaction tube 221 and equipped with a preheating section 222. Loaded in the reaction tube 221 is, for example, a nickel-based catalyst. The fluid passageway $230_1$ is connected to the reaction tube 221 via the preheating section 222. Also, a carbon dioxide recovery device 224 is connected to the preheating section 222 via a fluid passageway $230_2$.

A first reaction apparatus $240_1$ for synthesizing methanol is arranged downstream of the reformer 220 and connected to the reformer 220 via a fluid passageway $230_3$. The first reaction apparatus $240_1$ comprises a first pre-heater $241_1$ and a first reactor $243_1$ for synthesizing methanol. The synthetic gas coming from the first pre-heater $241_1$ is supplied to the first reactor $243_1$ via a first circulating passageway $242_1$. Arranged in the first reactor $243_1$ is a methanol synthesizing catalyst consisting of oxides of Cu, Zn, Al, Ga and M, which is at least one element selected from the alkaline earth metal elements and the rare earth elements, these Cu, Zn, Al, Ga and M being mixed at an atomic ratio of 100:10 to 200:1 to 20:1 to 20:0.1 to 20. A reactor housing a triple tube as shown in FIG. 3 can be used as the first reactor $243_1$. A heat exchanger 251, a heat recovery device 252 and a first compressor 253 are mounted to the fluid passageway $230_3$ interposed between the reformer 220 and the first pre-heater 241 in the order mentioned as viewed from the reformer 220. That portion of the fluid passageway $230_3$ which is interposed between the heat exchanger 251 and the heat recovery device 252 extends through the tube 212 of the moistening device 210.

A distillation column 260 is arranged downstream of the first reaction apparatus $240_1$ and is connected to the first reaction apparatus $240_1$ via a fluid passageway $230_4$. Incidentally, one end of the fluid passageway $230_4$ is connected to the bottom of the first reactor $243_1$. A first pre-heater $241_1$, a cooling device 271 and a gas-liquid separator 272 are mounted to the fluid passageway $230_4$ interposed between the first reactor $243_1$ of the first reaction apparatus $240_1$ and the distillation column 260 in the order mentioned as viewed from the first reactor $243_1$.

The gas-liquid separator 272 is connected to the fluid passageway $230_3$ at the inlet of the first pre-heater $241_1$ via a gas circulating passageway 273. A second gas compressor 274 is mounted to the gas circulating passageway 273. The gas circulating passageway 273 is connected to a second reaction apparatus $240_2$ for synthesizing methanol via a branched fluid passageway $230_5$. The carbon dioxide recovery device 224 is connected to the fluid passageway $230_5$ through a fluid passageway $230_6$. Further, a third gas compressor 275 is mounted to the fluid passageway $230_6$.

The second reaction apparatus $240_2$ comprises a second pre-heater $241_2$ and a second reactor $243_2$ for synthesizing methanol. A mixed gas consisting of the unreacted gas and carbon dioxide, coming from the second pre-heater $241_2$ is supplied to the second reactor $243_2$ through a second circulating passageway $242_2$. Loaded in the second reactor $243_2$ is a methanol synthesizing catalyst consisting of oxides of Cu, Zn, Al, Ga and M, which is at least one element selected from the alkaline earth metal elements and the rare earth elements, these Cu, Zn, Al, Ga and M being mixed at an atomic ratio of 100:10 to 200:1 to 20:1 to 20:0.1 to 20. A reactor housing a triple tube as shown in FIG. 3 can be used as the second reactor $243_2$. The bottom portion of the second reactor $243_2$ is connected to that portion of the fluid passageway $230_4$ which is interposed between the first pre-heater $241_1$ and the cooling device 271 through the fluid passageway $230_7$ extending through the second pre-heater $241_2$.

Figure 6:
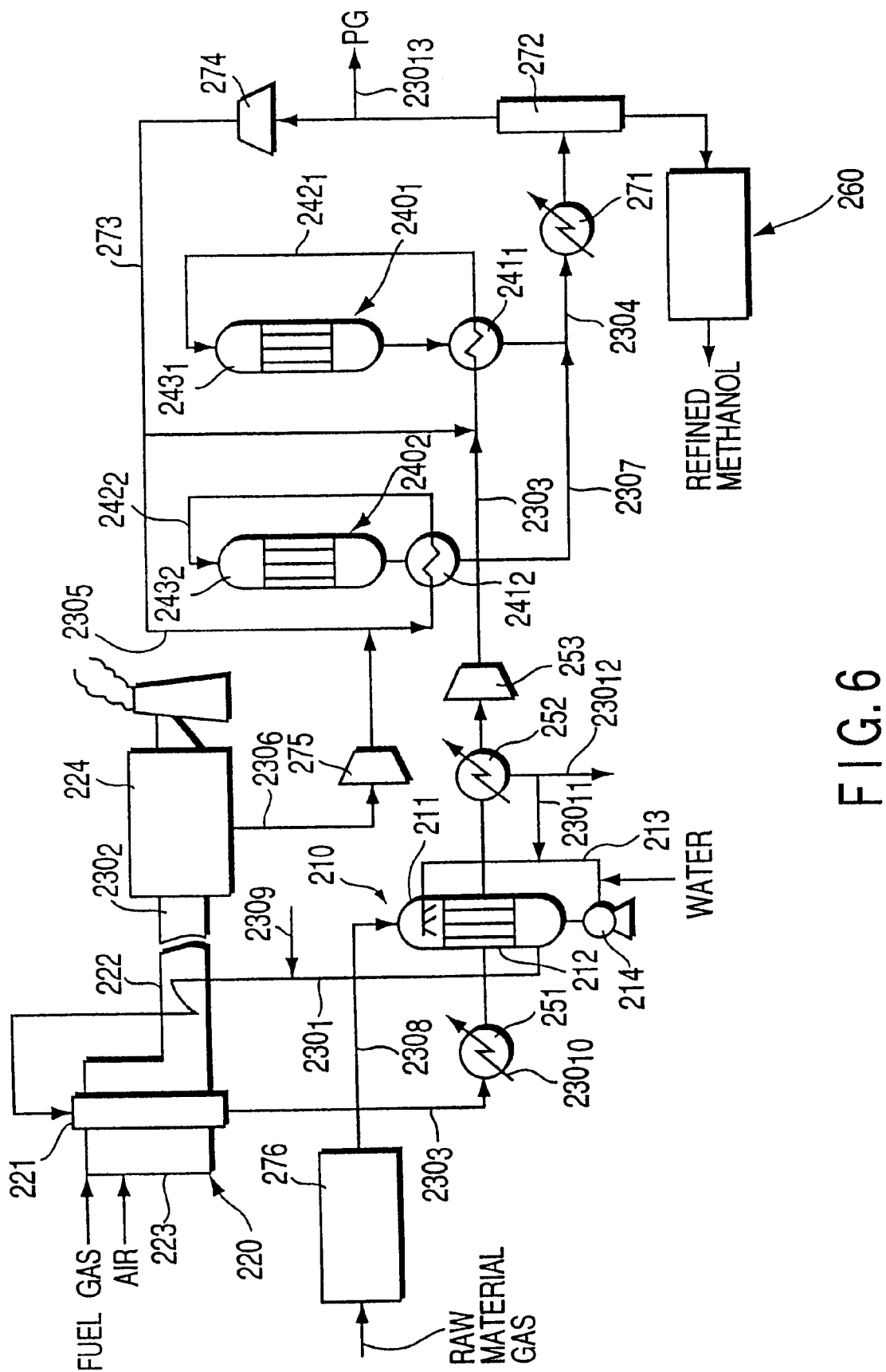
FIG. 6 schematically shows the methanol manufacturing plant used in Example 3 of the present invention.

The methanol manufacturing plant shown in FIG. 6 is operated as follows for manufacturing methanol.

In the first step, the preheated raw material gas containing hydrocarbon as a main component is desulfurized in the desulfurizing device 276 and, then, supplied to the loading layer 211 in the top portion of the heat exchange type moistening device 210 through a fluid passageway $230_8$. On the other hand, the pump 214 arranged below the moistening device 210 is operated in advance to circulate water from the bottom portion of the moistening device 210 to the top portion of the moistening device 210 through the circulating water passageway 213 so as to moisten the raw material gas supplied to the top portion of the moistening device 210. To be more specific, the raw material gas is brought into contact with the water supplied from the circulating water passageway 213 in the loading layer 211 and, then, exchanges heat within the tube 212 with the synthetic gas of a high temperature supplied from the reformer 220 so as to be heated and further moistened.

The moistened mixed gas is supplied through the fluid passageway $230_1$ into the steam reforming reaction tube 221 of the reformer 220. A required amount of the process steam is supplied to the moistened raw material gas through a fluid passageway $230_9$ while the raw material gas flows through the fluid passageway $230_1$ and, then, the raw material gas is supplied to the reaction tube 221 through the preheating section 222 positioned in the convection section of the reformer 220. The raw material gas containing hydrocarbon, e.g., methane gas, as a main component, which is supplied to the reaction tube 221 of the reformer 220, is subjected to steam reformation in the presence of a catalyst. As a result, the raw material gas is converted into a synthetic gas containing carbon monoxide, carbon dioxide and hydrogen. Since the steam reforming reaction is an endothermic reaction, a fuel gas and the air is supplied into the combustion device 223 of the reformer 220 so as to burn the fuel and, thus, to heat the inner space of the reaction tube 221 to, for example, 800 to 1,000° C. The waste combustion gas is supplied to the carbon dioxide recovery device 224 through the preheating section 222 and the fluid passageway $230_2$ so as to recover carbon dioxide.

The synthetic gas formed in the reformer 220 is supplied to the heat exchanger 251 through the fluid passageway $230_3$ and exchanges heat with a boiler water circulating through a fluid passageway $230_{10}$ to generate steam of a high pressure. Then, the synthetic gas is supplied to the outer fluid passageway of the tube 212 of the moistening device 210. The heat of the synthetic gas is partly recovered in the outer fluid passageway of the tube 212 so as to be utilized as a heat source of the moistening device 210.

The synthetic gas coming from the tube 212 is supplied to the heat recovery device 252 so as to be cooled to room temperature. In this step, the steam contained in the synthetic gas is condensed. The condensed water is partly supplied to the circulating water passageway 213 of the moistening device 210 through a fluid passageway $230_{11}$ so as to be utilized for the moistening of the raw material gas introduced into the moistening device 210. The remainder of the condensed water flows through a fluid passageway $230_{12}$ so as to be utilized as, for example, the process water.

The synthetic gas from which the condensed water has been separated is supplied to the first compressor 253 through the fluid passageway $230_3$ so as to be compressed to have a pressure adapted for the methanol synthesizing reaction, e.g., compressed to 50 to 150 atmospheres. The compressed synthetic gas is supplied to the first pre-heater $241_1$ of the first reaction apparatus $240_1$ through the fluid passageway $230_3$ so as to be preheated to a temperature adapted for the methanol synthesizing reaction, e.g., 200 to 300° C., and, then, further supplied to the first reactor $243_1$ loaded with the methanol synthesizing catalyst through the first circulating passageway $242_1$. Incidentally, the unreacted gas separated in the gas-liquid separator 272 described hereinlater is supplied to that portion of the fluid passageway $230_3$ which is positioned upstream of the first pre-heater $241_1$ so as to be mixed with the synthetic gas. The reactions (1) and (2) given previously are carried out in the first reactor $243_1$ so as to synthesize methanol. It is desirable to use the reactor housing a triple tube as shown in FIG. 3 as the first reactor $243_1$.

The gas formed in the first reactor $243_1$ is supplied to each of the first pre-heater $241_1$ and the cooling device 271 through the fluid passageway $230_4$ so as to be cooled to substantially room temperature. In this step, substantially all the methanol and water within the formed gas are condensed to form a liquid stream that flows into the gas-liquid separator 272. Within the gas-liquid separator 272, the unreacted gas is separated from the liquid crude methanol.

The unreacted gas is forwarded into the second gas compressor 274 through the gas circulating passageway 273 so as to be compressed to have a high pressure. Then, the compressed unreacted gas is circulated to the fluid passageway $230_3$ at the inlet of the first pre-heater $241_1$ so as to be supplied to the first reactor $243_1$ together with the synthetic gas. The unreacted gas is partly supplied to the second pre-heater $241_2$ of the second reaction apparatus $240_2$ for synthesizing methanol through the fluid passageway $230_5$ branched from the gas circulating passageway 273. At the same time, carbon dioxide is supplied from the carbon dioxide recovery device 224 to the fluid passageway $230_5$ via the fluid passageway $230_6$ mounted the third compressor 275. The compressed carbon dioxide supplied from the third compressor 275 to the fluid passageway $230_5$ is mixed with the unreacted gas, and the mixed gas is supplied to the second pre-heater $241_2$. The mixed gas is preheated within the second pre-heater $241_2$ to a temperature adapted for the methanol synthesizing reaction and, then, supplied to the second reactor $243_2$ loaded with a methanol synthesizing catalyst through the second circulating passageway $242_2$. In the second reactor $243_2$, carbon dioxide is mainly reacted with hydrogen to synthesize methanol.

The unreacted gas is partly supplied as a purge gas from the circulating gas passageway 273 through a fluid passageway $230_{13}$ so as to be used as a fuel for heating the reaction tube 221 of the reformer 220.

The gas formed in the second reactor $243_2$ flows through the fluid passageway $230_7$ and cooled by the second pre-heater $241_2$ mounted to the fluid passageway $230_7$ and, then, supplied to the fluid passageway $230_4$ so as to be combined with the gas formed in the first reactor $243_1$. The formed gas is further supplied to the cooling device 271 through the fluid passageway $230_4$ so as to be cooled to substantially room temperature. In this step, substantially all the methanol and water contained in the formed gas are condensed to form a liquid stream that flows into the gas-liquid separator 272. Within the gas-liquid separator 272, the liquid stream is separated into a liquid crude methanol and the unreacted gas. As already described, the unreacted gas is circulated to the synthetic gas supplied to the first reactor $243_1$, supplied to the second reactor $243_2$ and used as a purge gas that is used as a fuel in the reformer 220.

On the other hand, the crude methanol separated in the gas-liquid separator 272 is supplied to the distillation column 260 through the fluid passageway $230_4$ so as to refined into methanol of a high purity. The high purity methanol is withdrawn as a product to the outside of the system. Also, the water containing small amounts of high boiling point organic compounds, organic acids and traces of inorganic substances is discharged as a waste water to the outside of the system.

In Example 3, the methanol synthesizing step comprises the first and second reaction apparatus $240_1$ and $240_2$. The unreacted gas separated from the gas formed in the first reaction apparatus $240_1$ (and from the gas formed in the second reaction apparatus $240_2$) is supplied to the second reactor $243_2$ of the second reaction apparatus $240_2$ together with, for example, carbon dioxide recovered in the carbon dioxide recovery device 224 for synthesizing methanol. What should be noted is that the methanol yield can be increased in Example 3 by simply adding the second reaction apparatus without markedly modifying the methanol manufacturing plant.

It should also be noted that the unreacted gas is circulated to the fluid passageway $230_3$ positioned upstream of the first pre-heater $241_1$ of the first reaction apparatus $240_1$ so as to dilute the synthetic gas flowing through the fluid passageway $230_3$. As a result, the rate of heat generation in the methanol synthesizing step in the first reaction apparatus $240_1$ can be moderated so as to suppress deactivation of the methanol synthesizing catalyst loaded in the first reactor $243_1$.

Further, carbon dioxide recovered from the combustion gas discharged from the combustion device 22 of the reformer 220 (and/or from the boiler) can be supplied together with the unreacted gas to the second reactor $243_2$ of the second reaction apparatus $240_2$ so as to decrease the amount of carbon dioxide discharged from the methanol manufacturing plant to the outside. Naturally, the methanol manufacturing plant is rendered advantageous in economy when a tax or regulation of the carbon dioxide discharge is enforced in future.

Further, it is desirable to use a catalyst exhibiting a high durability when exposed to a synthetic gas containing a high concentration of carbon dioxide. In the case of using the particular catalyst, deactivation of the catalyst can be suppressed, making it possible to decrease the amount of the catalyst loaded in the reactor. To be more specific, it is desirable for the methanol synthesizing catalyst to consist of oxides of Cu, Zn, Al, Ga and M, which is at least one element selected from the alkaline earth metal elements and the rare earth elements, these Cu, Zn, Al, Ga and M being mixed at an atomic ratio of 100:10 to 200:1 to 20:1 to 20:0.1 to 20.

Incidentally, it is also possible in Example 3 to supply carbon dioxide recovered from the combustion gas discharged from, for example, the combustion device 223 of the reformer 220 (and/or from the boiler) to the fluid passageway $230_3$ positioned upstream of the first pre-heater $241_1$ of the first reaction apparatus $240_1$.

EXAMPLE 4

Figure 7:
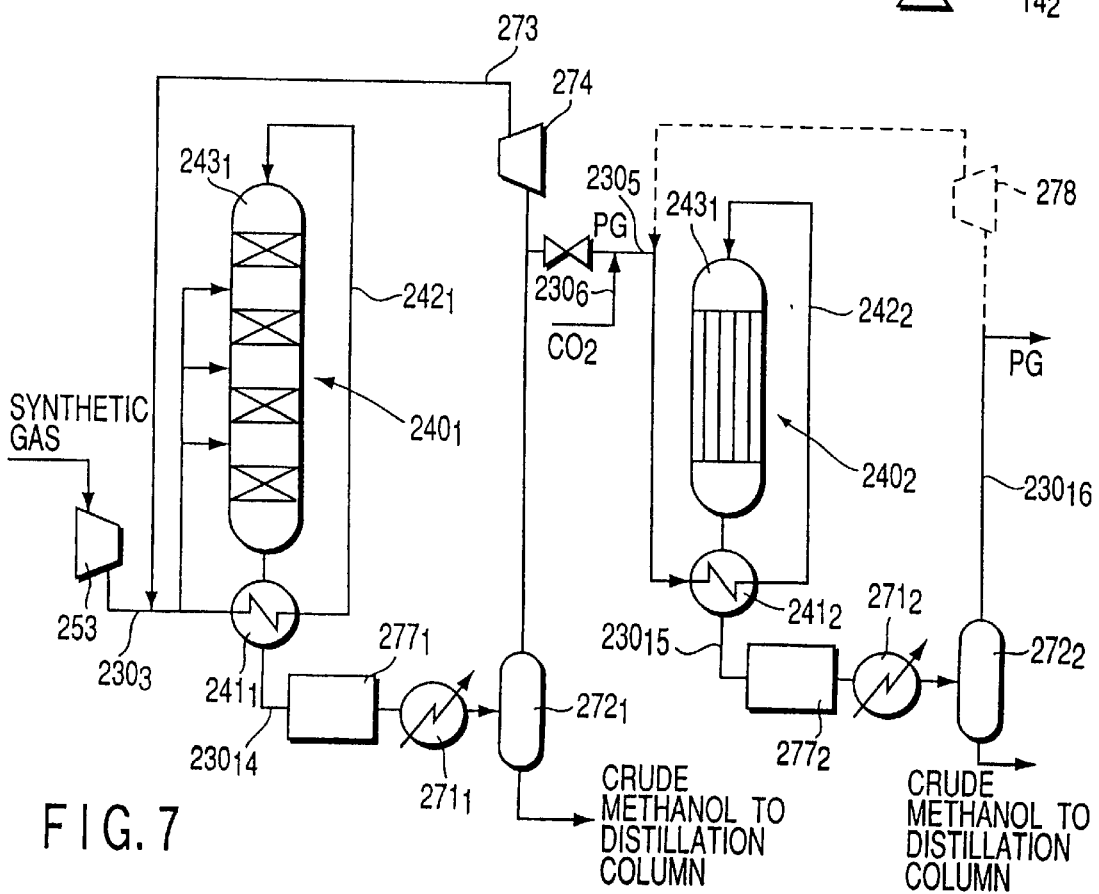
FIG. 7 schematically shows a gist portion of the methanol manufacturing plant used in Example 4 of the present invention.

Another example of manufacturing methanol according to the third embodiment of the present invention will be described in Example 4 with reference to FIG. 7 showing the gist portion of the methanol manufacturing plant. The reference numerals commonly used in FIGS. 6 and 7 represent the same members of the plant and, thus, explanation thereof will be omitted in the following description.

Specifically, FIG. 7 shows that a distillation column (not shown) is arranged downstream of the first reaction apparatus $240_1$ for synthesizing methanol, and the first reaction apparatus $240_1$ is connected to the distillation column via a fluid passageway $230_{14}$. The first reaction apparatus $240_1$ comprises a first pre-heater $241_1$ and a first reactor $243_1$. The synthetic gas coming from the first pre-heater $241_1$ is supplied to the first reactor $243_1$ through the first circulating passageway $242_1$. A methanol synthesizing catalyst substantially equal in composition to that used in Example 3 is loaded in the first reactor $243_1$. The fluid passageway $230_{14}$ noted above is connected to the bottom portion of the first reactor $243_1$. The first pre-heater $241_1$, the first heat recovery device $277_1$, the first cooling device $271_1$ and the first gas-liquid separator $272_1$ are mounted to the fluid passageway $230_{14}$ between the first reactor $240_1$ and the distillation column in the order mentioned as viewed from the first reactor $243_1$.

The first gas-liquid separator $272_1$ is connected to the fluid passageway $230_3$, through which flows the synthetic gas, at the inlet of the first pre-heater $241_1$ through the gas circulating passageway 273. The gas circulating passageway 273 is connected to the second reactor $240_2$ for synthesizing methanol through the branched fluid passageway $230_5$. A carbon dioxide recovery device (not shown) is connected to the fluid passageway $230_5$ through the fluid passageway $230_6$. Incidentally, a third gas compressor (not shown) is mounted to the fluid passageway $230_6$.

The distillation column is arranged downstream of the second reaction apparatus $240_2$ and connected to the second reaction apparatus $240_2$ through a fluid passageway $230_{15}$. The second reaction apparatus $240_2$ comprises a second pre-heater $241_2$ and a second reactor $243_2$ for synthesizing methanol. A mixed gas, consisting of the unreacted gas and carbon dioxide, coming from the second pre-heater $241_2$ is supplied to the second reactor $243_2$ through a second circulating passageway $242_2$. A methanol synthesizing catalyst substantially equal in composition to the catalyst used in Example 3 is loaded in the second reactor $243_2$. Incidentally, the fluid passageway $230_{15}$ is connected to the bottom portion of the second reactor $243_2$. The second pre-heater $241_2$, a second heat recovery device $277_2$, the second cooling device $271_2$, and the second gas-liquid separator $272_2$ are mounted to the fluid passageway $230_{15}$ interposed between the second reactor $243_2$ of the second reaction apparatus $240_2$ and the distillation column in the order mentioned as viewed from the second reactor $243_2$ of the second reaction apparatus $240_2$.

The methanol manufacturing plant shown in FIG. 7 is operated as follows for manufacturing methanol.

Specifically, the synthetic gas compressed to have a high pressure as in Example 3 is supplied to the first pre-heater $241_1$ of the first reaction apparatus $240_1$ for synthesizing methanol through the fluid passageway $230_3$ so as to be preheated to a temperature adapted for the methanol synthesizing reaction, e.g., 200 to 300° C., and, then, supplied through the first circulating passageway $242_1$ to the first reactor $243_1$ loaded with a methanol synthesizing catalyst. Incidentally, the unreacted gas separated in the first gas-liquid separator $272_1$ is supplied through the gas circulating passageway 273 to that portion of the fluid passageway $230_3$ which is positioned upstream of the first pre-heater $241_1$ so as to be mixed with the synthetic gas. The reactions (1) and (2) given previously are carried out in the first reactor $243_1$ to synthesize methanol.

The generated from the first reactor $243_1$ is supplied through the fluid passageway $230_{14}$ to each of the first pre-heater $241_1$, the first heat recovery device $277_1$, and the first cooling device $271_1$ so as to be cooled to substantially room temperature. In this step, almost all the methanol and water contained in the gas formed in the first reactor $243_1$ are condensed to form a liquid stream flowing into the first gas-liquid separator $272_1$. Then, the liquid stream is separated in the first gas-liquid separator $272_1$ into a liquid crude methanol and the unreacted gas.

The unreacted gas is forwarded through the gas circulating passageway 273 into the second gas compressor 274 so as to be compressed to have a high pressure and, then, further circulated through the gas circulating passageway 273 to fluid passageway $230_3$ at the inlet of the first pre-heater $241_1$. In this fashion, the unreacted gas is supplied together with the synthetic gas into the first reactor $243_1$.

The unreacted gas is partly supplied as a purge gas, the pressure of which is set lower than that within the first reactor $243_1$, into the second pre-heater $241_2$ of the second reaction apparatus $240_2$ for synthesizing methanol through the fluid passageway $230_5$ branched from the gas circulating passageway 273. At the same time, carbon dioxide is supplied from a carbon dioxide recovery device (not shown) to a third compressor (not shown) mounted to the fluid passageway $230_6$ so as to be compressed to have a high pressure and, then, supplied to the fluid passageway $230_5$ and mixed with the unreacted gas. The mixed gas is further supplied to the second pre-heater $241_2$ so as to be preheated to a temperature adapted for the methanol synthesizing reaction. Then, the preheated mixed gas is supplied through the second circulating passageway $242_2$ to the second reactor loaded with a methanol synthesizing catalyst. In the second reactor $243_2$, carbon dioxide mainly reacts with hydrogen to synthesize methanol.

The gas formed in the second reactor $243_2$ is supplied through the fluid passageway $230_{15}$ to each of the second pre-heater $241_2$, the second heat recovery device $277_2$ and the second cooling device $271_2$ mounted to the fluid passageway $230_{15}$ so as to be cooled to substantially room temperature. In this step, almost all the methanol and water contained in the gas formed in the second reactor $243_2$ are condensed to form a liquid stream flowing into the second gas-liquid separator $272_2$. The liquid stream is separated in the second gas-liquid separator $272_2$ into a liquid crude methanol and the unreacted gas. The unreacted gas flows as a purge gas through the fluid passageway $230_{16}$ so as to be utilized as a fuel for heating, for example, the reformer.

On the other hand, the crude methanol separated in the first and second gas-liquid separators $272_1$, $272_2$ is supplied to the distillation column (not shown) through fluid passageways $230_{14}$ and $230_{15}$ and, then, refined in the distillation column. The refined methanol of a high purity is withdrawn from the distillation column to the outside of the system. Also, water containing small amounts of high boiling point organic compounds, organic acids and traces of inorganic substances is discharged as a waste water to the outside of the system.

The methanol manufacturing process for Example 4 produces effects similar to those obtained in Example 3. It should also be noted that, in Example 4, the pressure of the unreacted gas supplied as a purge gas from the first gas-liquid separator $272_1$ to the second reaction apparatus $240_2$ for synthesizing methanol through the gas circulating passageway 273 is set lower than the pressure within the first reactor $243_1$. As a result, it is possible to suppress the compressing pressure of carbon dioxide to a level lower than the pressure within the first reactor $243_1$ in the step of supplying the carbon dioxide recovered in the carbon dioxide recovery device to the third compressor (not shown) mounted to the fluid passageway $230_6$ and, then, to the fluid passageway $230_5$. As a result, the compressing power can be made lower than that in Example 3.

In Example 4, it is also possible to supply the carbon dioxide recovered from the waste combustion gas discharged from, for example, the combustion device of the reformer (and/or boiler for steam generation) to the fluid passageway $230_3$ positioned upstream of the first pre-heater $241_1$ of the first reaction apparatus $240_1$.

Further, it is possible to compress the unreacted gas separated in the second gas-liquid separator $272_2$ in a fourth compressor 278 and, then, circulate the compressed unreacted gas to the fluid passageway $230_5$ through which flows a mixed gas consisting of the unreacted gas introduced from the first gas-liquid separator $272_1$ and carbon dioxide.

As described above, the present invention provides a methanol manufacturing method, which permits effectively utilizing the excess hydrogen in the gas formed in the reformer so as to increase the methanol yield without bringing about deactivation of the methanol synthesizing catalyst in the methanol synthesizing step, which permits effectively utilizing carbon dioxide so as to decrease the amount of carbon dioxide discharged to the outside, and which further permits decreasing the amount of steam supplied from the outside to the reformer.

It should also be noted that the moistening device consists of first stage and second stage moistening devices such that the waste water discharged from the distillation column is circulated to the first stage moistening device to which are supplied the raw material gas and carbon dioxide. As a result, the pH value of the waste water discharged from the distillation column is shifted toward the neutral or acidic side. It follows that the metal member of the first stage moistening device is prevented from being corroded by the alkali contained in the waste water discharged from the distillation column. In other words, the waste water discharged from the distillation column can be utilized effectively.

What should also be noted is that the methanol synthesizing process comprises the first reaction step and the second reaction step. In other words, the methanol yield can be increased by simply adding the second reaction step without markedly modifying the methanol manufacturing facilities.

Further, the recovered carbon dioxide can be utilized for synthesizing methanol at a low reaction pressure in the second reaction step so as to decrease the compressing power of carbon dioxide.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A method of manufacturing methanol, comprising the steps of:

supplying a raw material gas containing hydrocarbon as a main component and steam into a reformer, said raw material gas being supplied into said reformer through a moistening device, to carry out reaction between said hydrocarbon and steam to form a synthetic gas containing as main components hydrogen, carbon monoxide, and carbon dioxide;

performing reaction of said synthetic gas in the presence of a methanol synthesizing catalyst to synthesize a crude methanol; and distilling a liquid crude methanol recovered in said synthesizing process to separate the crude methanol into a waste liquid material and a refined methanol, said waste liquid material containing low boiling point organic compounds and high boiling point organic compounds, wherein carbon dioxide is supplied to at least one fluid passageway selected from the group consisting of a fluid passageway positioned upstream of said moistening device and another fluid passageway interposed between the moistening device and said reformer.

2. The method of manufacturing methanol according to claim 1, wherein said moistening device includes a first stage moistening device and a second stage moistening device arranged downstream of the first stage moistening device and upstream of the reformer such that the waste liquid material recovered in the distilling process is supplied to a circulating water passageway of the first stage moistening device, and a raw material gas containing hydrocarbon as a main component and carbon dioxide are supplied to a fluid passageway positioned upstream of the first stage moistening device.

3. The method of manufacturing methanol according to claim 2, wherein an additional carbon dioxide is supplied to at least one fluid passageway selected from the group consisting of a fluid passageway interposed between the first and second moistening devices and another fluid passageway interposed between the second stage moistening device and the reformer.

4. The method of manufacturing methanol according to claim 1, wherein the step of synthesizing the crude methanol is carried out by using a reaction apparatus comprising a reactor vertically partitioned by two partition plates into three chambers consisting of a synthetic gas supply chamber, a cooling medium circulating chamber and a residence chamber of the methanol-containing gas and a triple pipe extending through the two partition plates and consisting of an outer pipe, an intermediate pipe and an inner pipe that are concentrically arranged such that the upper end of the intermediate pipe is positioned lower than the upper end of the outer pipe, that the lower end of the inner pipe is positioned in a central portion of the intermediate pipe, that the inner pipe alone is open in the upper end of the triple pipe, and that an annular space is formed between the intermediate pipe and the outer pipe in the lower end of the triple pipe, the methanol synthesizing catalyst being loaded in the annular space.

5. The method of manufacturing methanol according to claim 1, wherein the methanol synthesizing catalyst consists of oxides of Cu, Zn, Al, Ga and M, wherein M is at least one element selected from alkaline earth metal and the rare earth metal, these Cu, Zn, Al, Ga and M being mixed at an atomic ratio (Cu:Zn:Al:Ga:M) of 100:(10 to 200):(1 to 20):(1 to 20):(0.1 to 20).

6. The method of manufacturing methanol according to any one of claims 1 to 5, wherein said carbon dioxide to be supplied is carbon dioxide recovered from at least one of the combustion gas for heating the reformer and the combustion gas of the boiler for steam generation.

7. A method of manufacturing methanol, comprising the steps of:

supplying a raw material gas containing hydrocarbon as a main component and steam into a reformer for the reaction to generate a synthetic gas containing as main components hydrogen, carbon monoxide and carbon dioxide;

performing reaction of the synthetic gas in the presence of a methanol synthesizing catalyst to synthesize a crude methanol; and distilling a liquid crude methanol recovered from the methanol synthesizing step to separate the crude methanol into a refined methanol and a waste liquid material containing low boiling point organic compounds and high boiling point organic compounds, wherein said methanol synthesizing step comprises a first reaction step and a second reaction step, reaction of the synthetic gas supplied through a synthetic gas supply passageway being carried out in the first reaction step in the presence of the methanol synthesizing catalyst, and wherein the formed liquid crude methanol containing unreacted gas is separated into a gaseous portion and a liquid portion, the liquid crude methanol is recovered, the unreacted gas is compressed and recycled to the synthetic gas supply passageway, and a part of the compressed unreacted gas is mixed with carbon dioxide, and the mixed gas is introduced into the second reaction step so as to carry out the reaction of the mixed gas in the presence of the methanol synthesizing catalyst to form a crude methanol.

8. The method of manufacturing methanol according to claim 7, wherein said synthetic gas contains hydrogen in a concentration higher than that required for synthesizing methanol by the reaction with carbon monoxide.

9. The method of manufacturing methanol according to claim 7, wherein an additional carbon dioxide is supplied to the inlet port of the first reaction step.

10. The method of manufacturing methanol according to claim 7, wherein at least one reaction step selected from the first reaction step and the second reaction step is carried out by using a reaction apparatus comprising a reactor vertically partitioned by two partition plates into three chambers consisting of a synthetic gas supply chamber, a cooling medium circulating chamber and a residence chamber of the methanol-containing gas and a triple pipe extending through the two partition plates and consisting of an outer pipe, an intermediate pipe and an inner pipe that are concentrically arranged such that the upper end of the intermediate pipe is positioned lower than the upper end of the outer pipe, that the lower end of the inner pipe is positioned in a central portion of the intermediate pipe, that the inner pipe alone is open in the upper end of the triple pipe, and that an annular space is formed between the intermediate pipe and the outer pipe in the lower end of the triple pipe, the methanol synthesizing catalyst being loaded in the annular space.

11. The method of manufacturing methanol according to claim 7, wherein the methanol synthesizing catalyst consists of oxides of Cu, Zn, Al, Ga and M, wherein M is at least one element selected from alkaline earth metal and the rare earth metal, these Cu, Zn, Al, Ga and M being mixed at an atomic ratio (Cu:Zn:Al:Ga:M) of 100:(10 to 200):(1 to 20):(1 to 20):(0.1 to 20).

12. The method of manufacturing methanol according to any one of claims 7 to 11, wherein said carbon dioxide to be supplied is carbon dioxide recovered from at least one of the combustion gas for heating the reformer and the combustion gas of the boiler for steam generation.

* * * * *